US006951855B2

(12) United States Patent
Bird

(10) Patent No.: US 6,951,855 B2
(45) Date of Patent: Oct. 4, 2005

(54) BENZOXAZINONE DERIVATIVES FOR USE IN THE TREATMENT OF ANGIOGENESIS

(75) Inventor: Thomas Geoffrey Colerick Bird, Reims (FR)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/475,051

(22) PCT Filed: Apr. 15, 2002

(86) PCT No.: PCT/GB02/01726

§ 371 (c)(1), (2), (4) Date: Oct. 17, 2003

(87) PCT Pub. No.: WO02/085868

PCT Pub. Date: Oct. 31, 2002

(65) Prior Publication Data

US 2004/0122006 A1 Jun. 24, 2004

(30) Foreign Application Priority Data

Apr. 23, 2001 (EP) ........................................... 01401031

(51) Int. Cl.[7] .................... C07D 265/36; A61K 31/538; A61P 35/00

(52) U.S. Cl. ..................................... 514/230.5; 544/105

(58) Field of Search ........................ 544/105; 514/230.5

(56) References Cited

FOREIGN PATENT DOCUMENTS

| | | |
|---|---|---|
| EP | 0 168 729 B1 | 1/1986 |
| EP | 0 434 440 B1 | 6/1991 |
| EP | 0 462 812 B1 | 12/1991 |
| EP | 0 462 813 B1 | 12/1991 |
| EP | 0 479 420 A2 | 4/1992 |
| EP | 0 485 111 A2 | 5/1992 |
| GB | 146078 | 5/1921 |
| JP | 6316568 | 11/1994 |
| WO | WO-94/26739 A1 | 11/1994 |
| WO | WO-95/30668 A1 | 11/1995 |

OTHER PUBLICATIONS

Kluge, M., et al., "First Syntheses of Natural Products with the 2,7–Dihydroxy–2H–1,4–benzoxazin–3(4H)–one Skeleton," J. Heterocyclic Chem., 32, 395–402 (1995).

Sumida, M., et al., "Synthesis of Novel Diphenyl Ether Herbicides," J. Agric. Food Chem., 43, 1929–1934 (1995).

Sumida, M., et al., "Protoporphyrinogen–IX Oxidase Inhibition of New Diphenyl Ethers," J. Pesticide Sci., 21, 317–321 (1996).

Hashimoto, Y., et al., "A Multi–Centered Electrophile Formed From a Unique Bioactive Cyclic Hydroxamic Acid, 4–Hydroxy–7–Methoxy–2H–1, 4–Benzoxazin–3(4H)–One," Tetrahedron, vol. 47(10/11), 1837–1860 (1991).

Ishizaki, T., et al., "Importance of the 2–Hydroxy Group for the Reactions of an Acetate of a Naturally Occurring Prohibitin, 4–Acetoxy–2–Hydroxy–2H–1, 4–Benzoxazin–3(4H)–One, with Nucleophiles," Heterocycles, vol. 34(4), 651–656 (1992).

Sastry, C. V. R., et al., "Synthesis & Anthelmintic Activity of Some New 6–(Aryllthio–/arylsulfonyl/substituted amino)–7–isothiocyanato–2H–1, 4–benzoxazin–3(4H)–ones," Indian Journal of Chemistry, vol. 27B, 290–292 (Mar. 1988).

Mohan, K. R., et al., "Synthesis and Physiological Activity of Some 2H–1,4–Benzoxazin–3–ones," Acta Ciencia Indica, vol. 10(3), 181–184 (1984).

Coutts, R. T., et al., "Acetylation and Acetoxylation of 4–Hydroxy–1,4–benzothianzin– and –benzoxazin–3(4H)–ones (Cyclic Hydroxamic Acids)," J. Chem. Soc., 15, 2696–2699 (1971).

*Primary Examiner*—Mark Berch
*Assistant Examiner*—Kahsay Habte

(57) ABSTRACT

This invention relates to novel compounds of Formula (I) for use as vascular damaging agents:

Formula (II)

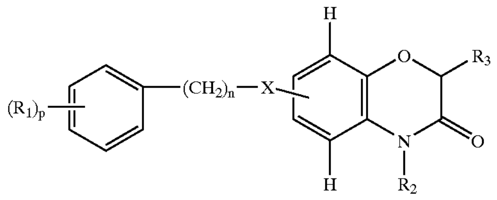

wherein: X is selected from: —O—, —S—, —S(O)—, —$S(O_2)$—, —$N(R_4)$— or —$N(R_4)CH_2C(O)$—; $R_1$ is independently selected from: amino, halo, hydroxy, —$OPO_3H_2$, $C_{1-4}$alkyl, $C_{1-4}$alkoxy, N-$C_{1-4}$alkylamino, N,N-di-$C_{1-4}$ alkanoylamino or $C_{1-4}$alkylthio wherein the amino group is optionally substituted by an amino acid residue and the hydroxy group is optionally esterified; $R_2$ is selected from: hydrogen or $C_{1-4}$alkyl; $R_3$ is selected from: hydrogen or $C_{1-4}$alkyl; $R_4$ is selected from: hydrogen or $C_{1-4}$alkyl; n is 0, 1 or 2; and p is 0, 1, 2 or 3; or a salt, pro-drug or solvate thereof. The invention also relates to methods for preparing compounds of Formula (I), to their use as medicaments (including methods for the treatment of angiogenesis or disease states associated with angiogenesis) and to pharmaceutical compositions containing compounds of Formula (I).

9 Claims, No Drawings

BENZOXAZINONE DERIVATIVES FOR USE IN THE TREATMENT OF ANGIOGENESIS

CROSS-REFERENCE TO RELATED APPLICATIONS

This application is a national stage filing under 35 U.S.C. 371 of International Application No. PCT/GB02/01726, filed Apr. 15, 2002, which claims priority from European Patent Application No. 01401031.8, filed Apr. 23, 2001, the specification of which is incorporated by reference herein. International Application No. PCT/GB02/01726 was published under PCT Article 21(2) in English.

1. Field of the Invention

This invention relates to vascular damaging agents and their uses. In particular it relates to certain compounds which may be of use as vascular damaging agents, to methods for preparing the compounds, to their use as medicaments (including methods for the treatment of angiogenesis or disease states associated with angiogenesis) and to pharmaceutical compositions containing them. The invention also relates to the use of such compounds in the manufacture of medicaments for the production of anti-angiogenic and/or anti-vascular effects.

2. Background of the Invention

Normal angiogenesis plays an important role in a variety of processes including embryonic development, wound healing and several components of female reproductive function. Undesirable or pathological angiogenesis has been associated with disease states including diabetic retinopathy, psoriasis, cancer, rheumatoid arthritis, atheroma, Kaposi's sarcoma and haemangioma (Fan et al, 1995, Trends Pharmacol. Sci. 16: 57–66; Folkman, 1995, Nature Medicine 1: 27–31). Formation of new vasculature by angiogenesis is a key pathological feature of several diseases (J. Folkman, New England Journal of Medicine 333, 1757–1763 (1995)). For example, for a solid tumour to grow it must develop its own blood supply upon which it depends critically for the provision of oxygen and nutrients; if this blood supply is mechanically shut off the tumour undergoes necrotic death. Neovascularisation is also a clinical feature of skin lesions in psoriasis, of the invasive pannus in the joints of rheumatoid arthritis patients and of atherosclerotic plaques. Retinal neovascularisation is pathological in macular degeneration and in diabetic retinopathy.

Reversal of neovascularisation by damaging the newly-formed vascular endothelium is therefore expected to have a beneficial therapeutic effect. Such vascular-damaging activity would clearly be of value in the treatment of disease states associated with angiogenesis such as cancer, diabetes, psoriasis, rheumatoid arthritis, Kaposi's sarcoma, haemangioma, acute and chronic nephropathies, atheroma, arterial restenosis, autoimmune diseases, acute inflammation, endometriosis, dysfunctional uterine bleeding and ocular diseases with retinal vessel proliferation.

Certain known compounds that cause selective destruction of tumour vasculature have been reported, in vitro and at non-cytotoxic concentrations, to cause effects on proliferating endothelial cells, ie, cell detachment [Blakey D C et al, *Proceedings of the American Association for Cancer Research,* 41, 329, 2000 abstract 2086] and changes in cell shape [Davis P D et al, *Proceedings of the American Association for Cancer Research,* 41, 329, 2000 abstract 2085; Chaplin D J & Dougherty G J, *Br J Cancer,* 80, Suppl 1, 57–64, 1999]. It can therefore be expected that these compounds will have damaging effects on newly-formed vasculature, for example the vasculature of tumours. It can reasonably be predicted, for example, that they will be capable of causing selective destruction of tumour vasculature, both in vitro and in vivo. Destruction of tumour vasculature in turn leads to a reduction in tumour blood flow and to tumour cell death due to starvation of oxygen and nutrients, ie, to anti-tumour activity [Davis P D et al; Chaplin D J & Dougherty G J; Blakey D C et al, all supra].

Compounds with this activity have also been described in International Patent Application WO 99/02166 (Angiogene Pharmaceuticals), International Patent Application WO 00/40529 (Angiogene Pharmaceuticals) and International Patent Application WO 00/41669 (Angiogene Pharmaceuticals).

We have identified a class of benzoxazionone compounds with therapeutic activity. Thus, according to the first feature of the present invention there is provided the use of a compound of Formula (I) as a medicament, wherein:

Formula (I)

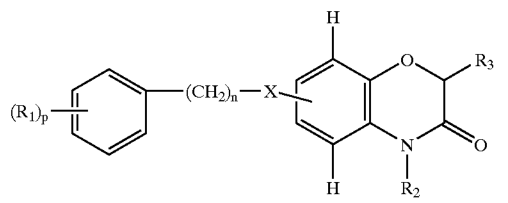

X is selected from: —O—, —S—, —S(O)—, —$S(O_2)$—, —$N(R_4)$— or —$N(R_4)CH_2C(O)$—;

$R_1$ is independently selected from: amino, halo, hydroxy, —$OPO_3H_2$, $C_{1-4}$alkyl, $C_{1-4}$alkoxy, N-$C_{1-4}$alkylamino, N,N-di-$C_{1-4}$alkylamino, $C_{1-4}$alkanoylamino or $C_{1-4}$alkylthio wherein the amino group is optionally substituted by an amino acid residue and the hydroxy group is optionally esterified;

$R_2$ is selected from: hydrogen or $C_{1-4}$alkyl;

$R_3$ is selected from: hydrogen or $C_{1-4}$alkyl;

$R_4$ is selected from: hydrogen or $C_{1-4}$alkyl;

n is 0, 1 or 2; and p is 0, 1, 2 or 3;

or a pharmaceutically-acceptable salt, pro-drug or solvate thereof.

According to a further aspect of the first feature of the invention there is provided a pharmaceutical composition comprising a compound of Formula (I) or pharmaceutically-acceptable salt, pro-drug or solvate thereof, and a pharmaceutically-acceptable excipient.

According to a further aspect of the first feature of the invention there is provided a pharmaceutical composition comprising a compound of Formula (I), or a pharmaceutically-acceptable salt, pro-drug or solvate thereof, in admixture with a pharmaceutically-acceptable diluent or carrier.

Compounds of Formula (I) have vascular damaging activity. Thus, according to the second feature of the present invention there is provided the use of a compound of Formula (I) or pharmaceutically-acceptable salt, pro-drug or solvate thereof, for the manufacture of a medicament to inhibit and/or reverse and/or alleviate symptoms of angiogenesis and/or any disease state associated with angiogenesis.

According to a further aspect of the second feature of the invention there is provided a method of treatment, in a warm-blooded animal, to inhibit and/or reverse and/or alleviate symptoms of angiogenesis and/or any disease state associated with angiogenesis comprising administering to said warm-blooded animal a therapeutically (including prophylactically) effective amount of a compound of Formula (I), or a pharmaceutically-acceptable salt, pro-drug or solvate thereof.

Preferably a warm-blooded animal is a human.

The invention also provides a class of novel benzoxazinone compounds. Thus, according to a third feature of the invention there is provided a compound of Formula (II), wherein:

Formula (II)

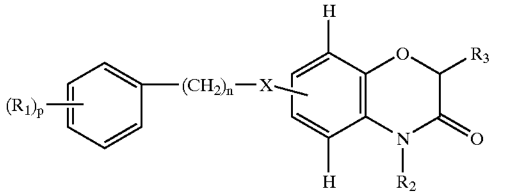

X is selected from: —O—, —S—, —S(O)—, —$S(O_2)$—, —$N(R_4)$— or —$N(R_4)CH_2C(O)$—;

$R_1$ is independently selected from: amino, halo, hydroxy, —$OPO_3H_2$, $C_{1-4}$alkyl, $C_{1-4}$alkoxy, N-$C_{1-4}$alkylamino, N,N-di-$C_{1-4}$alkylamino, $C_{1-4}$alkanoylamino or $C_{1-4}$alkylthio wherein the amino group is optionally substituted by an amino acid residue and the hydroxy group is optionally esterified;

$R_2$ is selected from: hydrogen or $C_{1-4}$alkyl;

$R_3$ is selected from: hydrogen or $C_{1-4}$alkyl;

$R_4$ is selected from: hydrogen or $C_{1-4}$alkyl;

n is 0, 1 or 2; and p is 0, 1, 2 or 3;

with the proviso that the following compounds are excluded:

6-benzyloxy-2H-1,4-benzoxazin-3(4H)-one;

7-benzyloxy-2H-1,4-benzoxazin-3)4H)-one;

2-methyl-7-benzyloxy-2H-1,4-benzoxazin-3(4H)-one;

2,4-dimethyl-7-benzyloxy-2H-1,4-benzoxazin-3(4H)-one;

2-methyl-7-(3,5-dichlorobenzyloxy)-2H-1,4-benzoxazin-3(4H)-one;

2,4-dimethyl-7-(3,5-dichlorobenzyloxy)-2H-1,4-benzoxazin-3(4H)-one;

7-phenylthio-2H-1,4-benzoxazin-3(4H)-one;

4-methyl-7-phenylthio-2H-1,4-benzoxazin-3(4H)-one;

4-methyl-7-phenylsulfinyl-2H-1,4-benzoxazin-3(4H)-one; and 6-phenylsulfonyl-2H-1,4-benzoxazin-3(4H)-one, or a salt, pro-drug or solvate thereof.

According to a further aspect of the third feature of the invention there is provided a compound of Formula (II), or a salt, pro-drug or solvate thereof, as defined above, with the proviso that (i) when the group —$(CH_2)_n$—X— is linked at the 6-position of the benzoxazinone ring, n is 0 or 1, X is —O— or —$S(O_2)$—, p is 0 and $R_2$ is hydrogen then $R_3$ cannot be hydrogen; and (ii) when the group —$(CH_2)_n$—X— is linked at the 7-position of the benzoxazinone ring, n is 0 or 1, X is —O—, —S— or —S(O)—, p is 0 or $(R_1)_p$ is 3,5-dichloro, and $R_2$ is hydrogen or methyl then $R_3$ cannot be hydrogen or methyl.

According to a further aspect of the third feature of the invention there is provided a compound of Formula (IIa), wherein:

Formula (IIa)

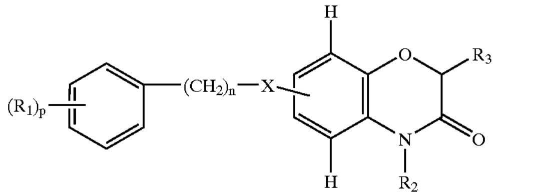

X is selected from: —O—, —S—, —S(O)—, —$S(O_2)$—, —$N(R_4)$— or —$N(R_4)CH_2C(O)$—;

$R_1$ is independently selected from: amino, hydroxy, —$OPO_3H_2$, $C_{1-4}$alkyl, $C_{1-4}$alkoxy, N-$C_{1-4}$alkylamino, N,N-di-$C_{1-4}$alkylamino, $C_{1-4}$alkanoylamino or $C_{1-4}$alkylthio wherein the amino group is optionally substituted by an amino acid residue and the hydroxy group is optionally esterified;

$R_2$ is selected from: hydrogen or $C_{1-4}$alkyl;

$R_3$ is selected from: hydrogen or $C_{1-4}$alkyl;

$R_4$ is selected from: hydrogen or $C_{1-4}$alkyl;

n is 0, 1 or 2; and p is 1, 2 or 3;

or a salt, pro-drug or solvate thereof.

According to a further aspect of the third feature of the invention there is provided a pharmaceutical composition comprising a compound of Formula (II) or Formula (IIa) or pharmaceutically-acceptable salt, pro-drug or solvate thereof, and a pharmaceutically-acceptable excipient.

According to a further aspect of the third feature of the invention there is provided a pharmaceutical composition comprising a compound of Formula (II), or Formula (IIa) or a pharmaceutically-acceptable salt, pro-drug or solvate thereof, in admixture with a pharmaceutically-acceptable diluent or carrier.

According to a further aspect of the third feature of the present invention there is provided the use of a compound of Formula (II) or Formula (IIa) or pharmaceutically-acceptable salt, pro-drug or solvate thereof, for the manufacture of a medicament to inhibit and/or reverse and/or alleviate symptoms of angiogenesis and/or any disease state associated with angiogenesis.

According to a further aspect of the third feature of the invention there is provided a method of treatment, in a warm-blooded animal, to inhibit and/or reverse and/or alleviate symptoms of angiogenesis and/or any disease state associated with angiogenesis comprising administering to said warm-blooded animal a therapeutically (including prophylactically) effective amount of a compound of Formula (II) or Formula (IIa), or a pharmaceutically-acceptable salt, pro-drug or solvate thereof.

Whilst pharmaceutically-acceptable salts of compounds of the invention are preferred, other non-pharmaceutically-acceptable salts of compounds of the invention may also be useful, for example in the preparation of pharmaceutically-acceptable salts of compounds of the invention.

For the avoidance of doubt when p is 0, all positions on the phenyl ring are substituted by hydrogen.

For the avoidance of doubt the use of the term $(R_1)_p$ when p is between 1 and 3, means that there are 1, 2 or 3 $R^1$ substituents on the phenyl ring, which when p is 2 or 3 can be the same group or different groups. For example, where $(R_1)_p$ is 3-chloro-4-methoxy then p is 2 and the phenyl ring has a chloro group at the 3-position and a methoxy group at the 4-position, in relation to the $—(CH_2)_nX—$ group.

The term halo refers to fluoro, chloro, bromo or iodo.

The term carbamoyl refers to the group $—CONH_2$.

An amino acid residue is defined as that derived from the coupling of an L-amino acid with an amino group via an amide bond. This bond can either be formed via a carboxylate group on the amino acid backbone or via a side chain carboxylate group, preferably via a carboxylate group on the amino acid backbone. Amino acid residues include those derived from natural and non-natural amino acids, preferably natural amino acids and include α-amino acids β-amino acids and γ-amino acids. For the avoidance of doubt amino acids include those with the generic structure:

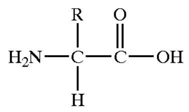

where R is the amino acid side chain. The definition of amino acid also includes amino acid analogues which have additional methylene groups within the amino acid backbone, for example β-alanine and amino acids which are not naturally occurring such as cyclohexylalanine.

Preferred amino acids include glycine, alanine, valine, leucine, isoleucine, methionine, proline, phenylalanine, tryptophan, serine, threonine, cysteine, tyrosine, asparaginine, glutamine, aspartic acid, glutamic acid, lysine, arginine, histidine, β-alanine and ornithine. More preferred amino acids include glutamic acid, serine, threonine, arginine, glycine, alanine, β-alanine and lysine. Especially preferred amino acids include glutamic acid, serine, and glycine.

Esterifying groups at $R_1$ are esterifying groups which increase the solubility of the molecule in water at a pH of approximately pH=7. Such groups include groups with ionisable groups, such as acidic functions or basic functions and groups containing a hydrophilic function. Basic functions include: amino, morpholino, piperidino, piperazino, pyrrolidino, amino acids and imidazolino. Acidic functions include: carboxy, sulphonic acid, phosphate, sulphate and acid mimetics such as tetrazolyl. Hydrophilic groups include hydroxyl.

Suitable $R_1$ groups wherein hydroxy is esterified include: $C_{1-6}$alkanoyloxy, arylcarbonyloxy, heterocyclylcarbonyloxy, heteroarylcarbonyloxy wherein the $R_1$ group is optionally substituted with between 1 and 3 groups selected from $C_{1-4}$alkyl, $C_{1-4}$alkanoyl, $C_{1-4}$alkanoyl$C_{1-4}$alkyl, $C_{1-4}$alkanoylheterocyclyl, hydroxy, hydroxy$C_{1-4}$alkyl, carboxy, carboxyphenyl, phosphono, phosphono$C_{1-4}$alkyl, amino, amino$C_{1-4}$alkyl, N-$C_{1-4}$-alkylamino, N,N-di$C_{1-4}$alkylamino, carbamoyl, carbamoyl$C_{1-4}$alkyl, heterocyclyl, heterocyclyl$C_{1-4}$alkyl, heterocyclylcarbonyl, heterocycl$C_{1-4}$alkanoylamino, carbamoylheterocyclyl, [wherein optional substituents comprising heterocyclyl are optionally further substituted by $C_{1-4}$alkyl, hydroxy$C_{1-4}$alkyl, $C_{1-4}$alkoxy$C_{1-4}$alkyl, $C_{1-4}$alkanoyl and formyl, wherein the carbamoyl and amino optional substituents are optionally further N-substituted by $C_{1-4}$alkyl, di-$C_{1-4}$alkyl, hydroxy$C_{1-4}$alkyl, di-(hydroxy$C_{1-4}$ alkyl), carboxy$C_{1-4}$alkyl, and wherein the amino group is optionally substituted by an amino acid residue] with the proviso that when $R_1$ is $C_{1-6}$alkanoyloxy or arylcarbonyloxy $R_1$ is not unsubstituted and $R_1$ is not substituted by $C_{1-4}$-alkyl.

More preferred $R_1$ groups wherein hydroxy is esterfied include: carboxypentanoyloxy, 4-carboxyphenylpropanoyloxy, 4-(N-methylpiperizin-1-ylethyl)phenylcarbonyloxy, 4-(piperizin-1-ylethyl)phenylcarbonyloxy, 4-[N-di-(hydroxyethyl)aminomethyl]phenylcarbonyloxy, 3-(N-acetylpiperizin-1-ylethyl)phenylcarbonyloxy, 3-[N-di-(hydroxyethyl)aminomethyl]phenylcarbonyloxy, 4-(N-methylpiperizin-1-ylpropanoylamino)phenylcarbonyloxy, N-methylpiperizin-1-ylcarbonylpropanoyloxy, N-di-(hydroxyethyl)aminocarbonylpropanoyloxy, piperizin-1-ylcarbonylpropanoyloxy, (N-acetylpiperizin-1-yl)carbonylpropanoyloxy, (N-di-(hydroxyethyl)aminocarbonylpropanoyloxy, and 4-(piperizin-1-ylmethyl)phenylcarbonyloxy.

Further preferred $R_1$ groups wherein hydroxy is esterified include: 4-(N-methylpiperizin-1-ylpropanoylamino)phenylcarbonyloxy, N-methylpiperizin-1-ylcarbonylpropanoyloxy and N-di-(hydroxyethyl)aminocarbonylpropanoyloxy.

In this specification the generic term 'alkyl' includes both straight-chain and branched-chain alkyl groups. However references to individual alkyl groups such as 'propyl' are specific for the straight-chain version only and references to individual branched-chain alkyl groups such as 'isopropyl' are specific for the branched-chain version only. An analogous convention applies to other generic terms. Examples of $C_{1-4}$alkyl include methyl, ethyl, propyl, isopropyl, sec-butyl and tert-butyl; Examples of $C_{1-4}$alkoxy$C_{1-4}$alkyl include propxomethyl, butoxyethyl or methoxyethyl; examples of amino$C_{1-4}$alkyl include aminomethyl, aminoethyl or aminopropyl; examples of carboxy$C_{1-4}$alkyl include carboxymethyl, carboxyethyl or carboxypropyl; example of carbamoyl$C_{1-4}$alkyl include carbamoylethyl or carbamoylpropyl; examples of heterocyclyl$C_{1-4}$alkyl include piperazinylmethyl, piperazinylethyl, morpholinylmethyl or morpholinylethyl; examples of $C_{1-4}$alkoxy include methoxy, ethoxy and propoxy; examples of N-$C_{1-4}$alkylamino include N-methylamino and N-ethylamino; examples of N,N-di-$C_{1-4}$ alkylamino include N,N-dimethylamino, N,N-diethylamino and N-methyl-N-ethylamino; examples of hydroxy$C_{1-4}$alkyl include hydroxyethyl or hydroxypropyl; examples of $C_{1-4}$alkanoyl include formyl or propanoyl; examples of $C_{1-6}$alkanoyloxy include propanoyloxy or butanoyloxy; examples of $C_{1-4}$alkanoyl$C_{1-4}$alkyl include formylethyl or propanoylmethyl; examples of $C_{1-4}$alkanoylamino include acetylamino, propanoylamino and butanoylamino; examples of heterocycl$C_{1-4}$ alkanoylamino include piperizinylpropanoylamino or piperidinylacetylamino; examples of $C_{1-4}$alkanoylheterocyclyl include formylpiperidinyl, acetylpiperidinyl, formylpiperazinyl or acetylpiperazinyl; examples of arylcarbonyloxy include phenylcarbonyloxy; examples of heterocyclylcarbonyl include piperazinylcarbonyl or piperidinylcarbonyl; examples of heterocyclylcarbonyloxy include piperazinylcarbonyloxy, piperidinylcarbonyloxy or morpholinylcarbonyloxy; examples of heteroarylcarbonyloxy include pyridinylcarbonyloxy or pyrimidinylcarbonyloxy; examples of $C_{1-4}$alkylthio include methylsulfanyl, ethylsulfanyl and butylsulfanyl; examples of phosphone$C_{1-4}$alkyl include phosphonopropyl, phosphonoethyl or phosphonomethyl; and examples of carbamoylheterocyclyl include carbamoylpiperazinyl or carbamoylpiperidinyl.

It is to be understood that, insofar as certain of the compounds in the different features of the invention may exist in optically active or racemic forms by virtue of one or more asymmetric carbon atoms, the invention includes in its definition any such optically active or racemic form which possesses the property of inhibiting and/or reversing and/or alleviating the symptoms of angiogenesis and/or any disease states associated with angiogenesis. The synthesis of optically active forms may be carried out by standard techniques of organic chemistry well known in the art, for example by synthesis from optically active starting materials or by resolution of a racemic form. Similarly, activity of these compounds may be evaluated using the standard laboratory techniques referred to hereinafter.

The invention also relates to any and all tautomeric forms of the compounds of the different features of the invention that possess the property of inhibiting and/or reversing and/or alleviating the symptoms of angiogenesis and/or any disease states associated with angiogenesis.

It will also be understood that certain compounds of the present invention may exist in solvated, for example hydrated, as well as unsolvated forms. It is to be understood that the present invention encompasses all such solvated forms which possess the property of inhibiting and/or reversing and/or alleviating the symptoms of angiogenesis and/or any disease states associated with angiogenesis.

The compounds of Formula (I), Formula (II) or Formula (IIa) may be administered in the form of a pro-drug which is broken down in the human or animal body to give a compound of the Formula (I), Formula (II) or Formula (IIa) respectively. Examples of pro-drugs include in-vivo hydrolysable esters of a compound of the Formula (I), Formula (II) or Formula (IIa).

Various forms of pro-drugs are known in the art. For examples of such pro-drug derivatives, see:

a) Design of Prodrugs, edited by H. Bundgaard, (Elsevier, 1985) and Methods in Enzymology, Vol. 42, p. 309–396, edited by K. Widder, et al. (Academic Press, 1985);

b) A Textbook of Drug Design and Development, edited by Krogsgaard-Larsen and H. Bundgaard, Chapter 5 "Design and Application of Prodrugs", by H. Bundgaard p. 113–191 (1991);

c) H. Bundgaard, Advanced Drug Delivery Reviews, 8, 1–38 (1992);

d) H. Bundgaard, et al., Journal of Pharmaceutical Sciences, 77, 285 (1988); and e) N. Kakeya, et al., Chem Pharm Bull, 32, 692 (1984).

An in-vivo hydrolysable ester of a compound of the Formula (I), Formula (II) or Formula (IIa) containing a carboxy or a hydroxy group is, for example, a pharmaceutically-acceptable ester which is hydrolysed in the human or animal body to produce the parent acid or alcohol. Suitable pharmaceutically-acceptable esters for carboxy include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters, for example 5-methyl-1,3-dioxolen-2-onylmethyl; and $C_{1-6}$alkoxycarbonyloxyethyl esters.

An in-vivo hydrolysable ester of a compound of the Formula (I), Formula (II) or Formula (IIa) containing a hydroxy group includes inorganic esters such as phosphate esters (including phosphoramidic cyclic esters) and α-acyloxyalkyl ethers and related compounds which as a result of the in-vivo hydrolysis of the ester breakdown to give the parent hydroxy group/s. Examples of α-acyloxyalkyl ethers include acetoxymethoxy and 2,2-dimethylpropionyloxy-methoxy. A selection of in-vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl.

A suitable-pharmaceutically-acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of a benzoxazinone derivative of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

A preferred group of values of X in each feature of the invention is —O—, —S—, —$S(O_2)$—, or —$N(R_4)$–. Preferably X is —O—, —S— or —$N(R_4)$—. Most preferably X is —O— or —S—. In another embodiment of the invention X is: —O—, —S—, —$N(R_4)$— or —$N(R_4)CH_2C(O)$—;

A preferred group of values of $R_1$ in each feature of the invention is amino, hydroxy, methyl, $C_{1-4}$alkoxy or —$OPO_3H_2$ wherein the amino group is optionally substituted by an amino acid and the hydroxy group is optionally esterified. Preferably $R_1$ is amino, hydroxy, methoxy, α-glutamylamino, serylamino, alanylamino or —$OPO_3H_2$, wherein the hydroxy group is optionally esterified. More preferably $R_1$ is amino, hydroxy, methoxy, α-glutamylamino, serylamino, or —$OPO_3H_2$. In another embodiment of the invention $R^1$ is $C_{1-4}$alkyl, $C_{1-4}$alkoxy, $C_{1-4}$alkanoylamino, halo, amino, hydroxy, α-glutamylamino, or —$OPO_3H_2$.

A preferred group of values of $R_2$ in each feature of the invention is hydrogen, methyl or ethyl; Preferably $R_2$ is hydrogen.

A preferred group of values of $R_3$ in each feature of the invention is hydrogen, methyl or ethyl. Preferably $R_3$ is hydrogen.

A preferred group of values of $R_4$ in each feature of the invention is hydrogen, methyl or ethyl. Preferably $R_4$ is hydrogen.

A preferred group of compounds of each feature of the invention, comprise compounds wherein:

X is —O—;

or a salt, pro-drug or solvate thereof.

A further preferred group of compound of each feature of the invention, comprise compounds wherein:

X is —$N(R_4)$—, preferably —NH—;

or a salt, pro-drug or solvate thereof.

A further preferred group of compounds of each feature of the invention, comprise compounds wherein:

X is —S—, —S(O)— or —$S(O_2)$—, preferably —S—;

or a salt, pro-drug or solvate thereof.

A further preferred group of compounds of each feature of the invention, comprise compounds wherein:

X is —$N(R_4)CH_2C(O)$—;

or a salt, pro-drug or solvate thereof.

A further preferred group of compounds of each feature of the invention, comprise compounds wherein:

$R_1$ is amino, $C_{1-4}$alkoxy, hydroxy or —$OPO_3H_2$, wherein the amino group is optionally substituted by an amino acid residue and the hydroxy group is optionally esterified;

or a salt, pro-drug or solvate thereof.

Particular compounds of each feature of the invention include:

7-[(2-aminophenyl)sulfanyl]-2H-1,4-benzoxazin-3(4H)-one;

7-(3-aminophenoxy)-2H-1,4-benzoxazin-3(4H)-one; and

6-[2-(4-toluidino)acetyl]-2H-1,4-benzoxazin-3(4H)-one;

or a salt, pro-drug or solvate thereof.

More particular compounds of each feature of the invention include:

7-[(3-aminophenyl)sulfanyl]-2H-1,4-benzoxazin-3(4H)-one; and

7-[(4-hydroxyphenyl)sulfanyl]-2H-1,4-benzoxazin-3(4H)-one;

or a salt, pro-drug or solvate thereof.

A compound of the invention or a pharmaceutically-acceptable salt, pro-drug or solvate thereof, may be prepared by any process known to be applicable to the preparation of chemically related compounds. Such processes, when used to prepare a compound of the invention or a salt, pro-drug or solvate thereof, are provided as a further feature of the invention and are illustrated by the following representative examples in which $R_1$, $R_2$, $R_3$, $R_4$, X, n and p have the same meaning as herein before defined. The reader is referred to Advanced Organic Chemistry, 4th Edition, by Jerry March, published by John Wiley & Sons 1992, for general guidance on reaction conditions and reagents. The reader is referred to Protective Groups in Organic Synthesis 2nd Edition, by Green et al, published by John Wiley & Sons for general guidance on protecting groups.

Thus, according to the fourth feature of the invention there is provided a process for preparing a compound of Formula (I), Formula (II) or Formula (IIa), or salt, pro-drug or solvate thereof, which process (wherein n, p, X, $R_1$, $R_2$, $R_3$, and $R_4$ are unless otherwise specified as defined in Formula (I), Formula (II) or Formula (IIa) respectively comprises:

a) for compounds of Formula (I), Formula (II) or Formula (IIa) wherein X is —O—, —S— or —$N(R_4)$—, reacting a compound of Formula (A) with a compound of Formula (B), Formula (A)

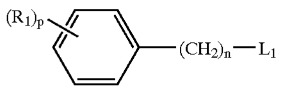

Formula (B)

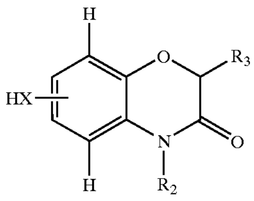

wherein $L_1$ is a leaving group;

b) for compounds of Formula (I), Formula (II) or Formula (IIa) wherein $R_2$ is hydrogen, reduction of a compound of Formula (C), wherein $R_6$ is hydrogen or an alkyl chain, Formula (C)

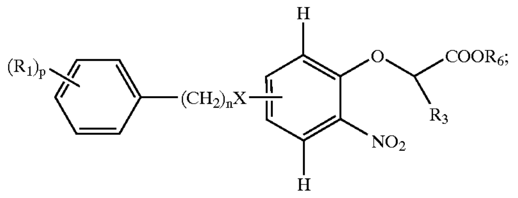

c) for compounds of Formula (I), Formula (II) or Formula (IIa) wherein $R_2$ is $C_{1-4}$alkyl, reacting a compound of Formula (I) wherein $R_2$ is hydrogen with a suitable alkylhalide;

d) for compounds of Formula (I), Formula (II) or Formula (IIa) wherein X is —S(O)—, —$S(O_2)$—, oxidising a compound of Formula (D), Formula (D)

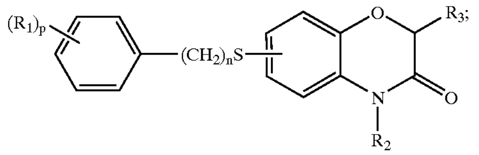

e) for compounds of Formula (I), Formula (II) or Formula (IIa) wherein X is —$N(R_4)CH_2C(O)$—, reacting a compound of Formula (E) with a compound of Formula (F), Formula (E)

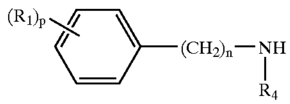

Formula (F)

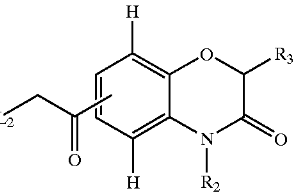

wherein $L_2$ is a leaving group; and thereafter if necessary:

i) converting a compound of the Formula (I), Formula (II) or Formula (IIa) into another compound of the Formula (I), Formula (II) or Formula (IIa) respectively;

ii) removing any protecting groups;

iii) forming a salt, pro-drug or solvate.

According to a further aspect of the fourth feature of the invention there is provided the processes a), b), c), d) and e) described above for the preparation of compounds of the Formula (I), or a salt, pro-drug or solvate thereof.

Specific reaction conditions for the above reactions are as follows:

a) Compounds of Formula (A) and compound of Formula (B) can be reacted together in an organic solvent, at a temperature between room temperature and about 80° C., optionally in the presence of a base such as sodium hydride, potassium carbonate or triethylamine.

Process b) The conditions for reduction of a compound of Formula (C) are well known in the art. Examples of reducing agents include hydrogen and a hydrogenation catalyst (for example palladium on carbon), zinc or iron in acetic acid or hydrochloric acid. The reaction is preferably carried out in the presence of zinc with acetic acid, and at a temperature in the range of 0–80° C., preferably at or near room temperature.

Process c) Compounds of Formula (I), Formula (II) or Formula (IIa) wherein $R_2$ is hydrogen and a suitable alkylhalide may be reacted together in a suitable organic solvent such as DMF or DMSO, in the presence of a base, such as sodium hydride or potassium carbonate at a temperature between about room temperature to about 80° C.

Process d) The oxidization of a compound of Formula (D) is well known in the art, for example, reaction with metachloroperbenzoic acid (MCPBA) in the presence of a suitable solvent such as dichloromethane at ambient temperature. If an excess of MCPBA is used a compound of Formula (I), Formula (II) or Formula (IIa) wherein X is —$S(O_2)$— is obtained.

Process e) Compounds of Formula (E) and Formula (F) can be reached together in the presence of an organic solvent, preferably acetone, in the presence of a base, preferably potassium carbonate, at a temperature between about room temperature and 80° C.

Intermediates for the processes a), b), c) and d) can be prepared as outlined in Scheme 1, wherein P is a protecting group, using the following reaction conditions:

Reaction Conditions (i) Reaction with ethyl bromoacetate in an organic solvent such as DMF or acetone, in the presence of a base such as sodium hydride or potassium carbonate at a temperature between approximately room temperature and approximately 80° C.

Reaction Conditions (ii) Reduction using a suitable reducing agent such as hydrogen and a hydrogenation catalyst (for example palladium on carbon), iron or zinc in acetic acid or hydrochloric acid.

Reaction Conditions (iii) Reaction conditions for the removal of a protecting group are well know in the art.

The compounds used as starting points for the reactions described above are commercially available or they are known compounds or they are prepared by processes known in the art.

Scheme 1

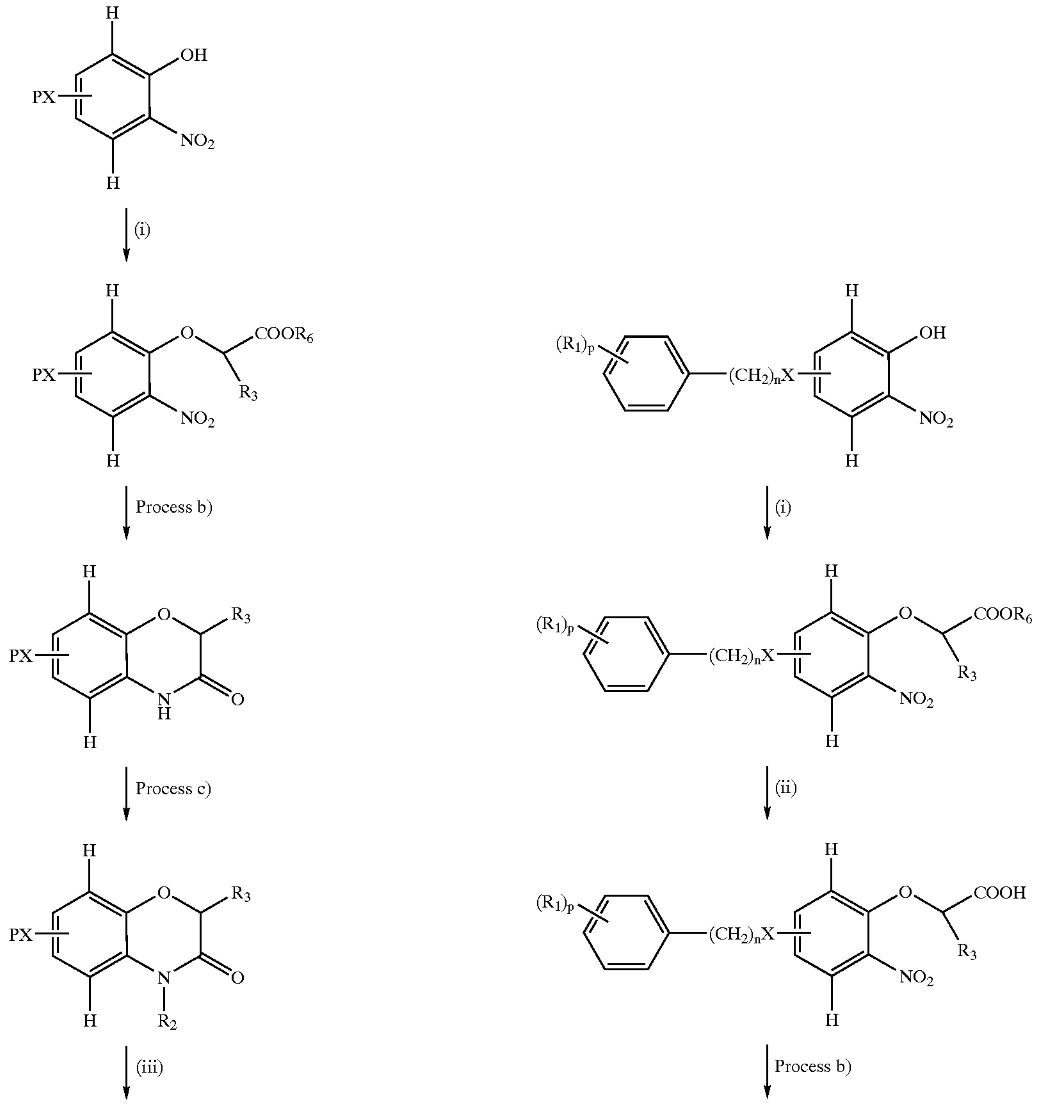

-continued

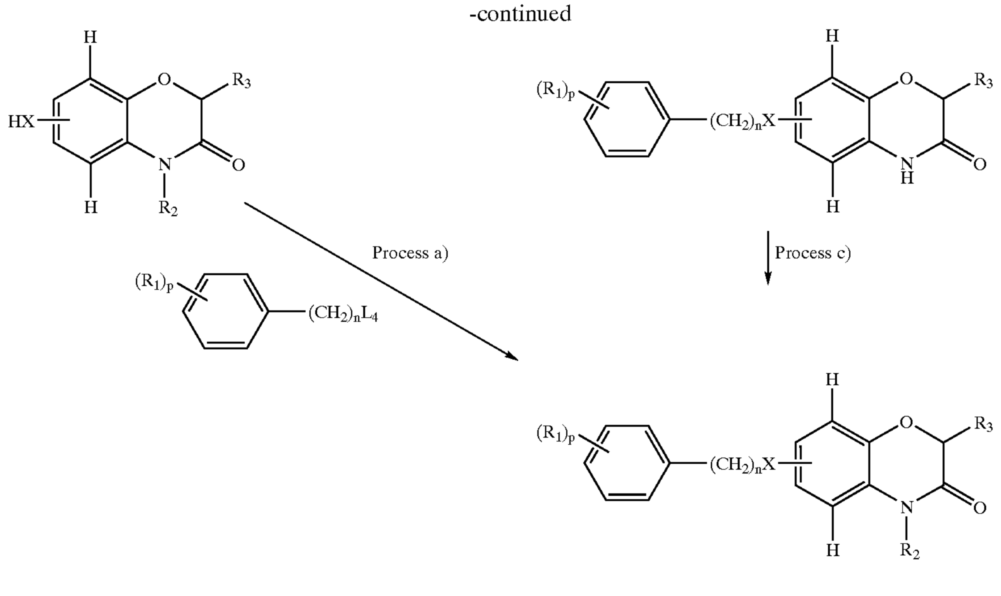

It will also be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1991). Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or form example a benzyl group which may be removed, for example, by hydrogenation over a catalyst such as palladium-on-carbon.

The protecting groups may be removed at any convenient stage in the synthesis using conventional techniques well known in the chemical art.

In order to use a compound of the Formula (I), Formula (II) or Formula (IIa), or a pharmaceutically-acceptable salt, pro-drug or solvate thereof, for the therapeutic treatment (including prophylactic treatment) of mammals including humans, it is normally formulated in accordance with standard pharmaceutical practice as a pharmaceutical composition.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically-acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxyethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically-acceptable, vehicle or diluent using conventional procedures well known in the art.

Compositions for administration by insufflation may be in the form of a finely divided powder containing particles of average diameter of, for example, 30 $\mu$m or much less, the powder itself comprising either active ingredient alone or diluted with one or more physiologically-acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurised aerosol arranged to disperse the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The size of the dose for therapeutic or prophylactic purposes of a compound of the Formula (I), Formula (II) or Formula (IIa) will naturally vary according to the nature and severity of the conditions, the age and sex of the animal or patient and the route of administration, according to well known principles of medicine.

In using a compound of the Formula (I), Formula (II) or Formula (IIa) for therapeutic or prophylactic purposes it will generally be administered so that a daily dose in the range of, for example, 0.5 mg to 75 mg per kg body weight is received, given if required in divided doses. In general lower doses will be administered when a parenteral route is employed. Thus, for example, for intravenous administration, a dose in the range of, for example, 0.5 mg to 20 mg per kg body weight will generally be used. Intravenous administration is however preferred, typically, intravenous doses of about 10 mg to 500 mg per patient of a compound of this invention.

The compounds of this invention may be used in combination with other drugs and therapies used to inhibit and/or reverse and/or alleviate symptoms of angiogenesis and/or any disease state associated with angiogenesis. Examples of such disease states includes: cancer, diabetes, psoriasis, rheumatoid arthritis, Kaposi's sarcoma, haemangioma, acute and chronic nephropathies, atheroma, arterial restenosis, autoimmune diseases, acute inflammation, endometriosis, dysfunctional uterine bleeding and ocular diseases with retinal vessel proliferation.

If formulated as a fixed dose such combination products employ the compounds of this invention within the dosage range described herein and the other pharmaceutically-active agent within its approved dosage range. Sequential use is contemplated when a combination formulation is inappropriate.

In the field of medical oncology examples of such combinations include combinations with the following categories of therapeutic agent:

i) anti-angiogenic agents that work by different mechanisms from the compounds of Formula (I), Formula (II) or Formula (IIa) (for example linomide, inhibitors of integrin $\alpha v\beta 3$ function, angiostatin, endostatin, razoxin, thalidomide) and including vascular endothelial growth factor (VEGF) receptor tyrosine kinase inhibitors (RTKIs) (for example those described in international patent applications publication nos. WO-97/22596, WO-97/30035, WO-97/32856 and WO-98/13354, the entire disclosure of which documents is incorporated herein by reference);

ii) cytostatic agents such as anti-oestrogens (for example tamoxifen, toremifene, raloxifene, droloxifene, iodoxyfene), progestogens (for example megestrol acetate), aromatase inhibitors (for example anastrozole, letrazole, vorazole, exemestane), anti-progestogens, anti-androgens (for example flutamide, nilutamide, bicalutamide, cyproterone acetate), LHRH agonists and antagonists (for example goserelin acetate, luprolide), inhibitors of testosterone $5\alpha$-dihydroreductase (for example finasteride), anti-invasion agents (for example metalloproteinase inhibitors like marimastat and inhibitors of urokinase plasminogen activator receptor function) and inhibitors of growth factor function, (such growth factors include for example epidermal growth factor (EGF), platelet derived growth factor and hepatocyte growth factor such inhibitors include growth factor antibodies, growth factor receptor antibodies, tyrosine kinase inhibitors and serine/threonine kinase inhibitors);

iii) biological response modifiers (for example interferon);

iv) antibodies (for example edrecolomab); and v) anti-proliferative/anti-neoplastic drugs and combinations thereof, as used in medical oncology, such as anti-metabolites (for example anti-folates like methotrexate, fluoropyrimidines like 5-fluorouracil, purine and adenosine analogues, cytosine arabinoside); anti-tumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide, nitrosoureas, thiotepa); anti-mitotic agents (for example vinca alkaloids like vincristine and taxoids like taxol, taxotere); enzymes (for example asparaginase); thymidylate synthase inhibitors (for example raltitrexed); topoisomerase inhibitors (for example epipodophyllotoxins like etoposide and teniposide, amsacrine, topotecan, irinotecan).

The compounds of the invention may also be used in combination with surgery or radiotherapy.

According to the fifth feature of the present invention there is provided a compound of Formula (I), Formula (II) or Formula (IIa), or pharmaceutically-acceptable salt, pro-drug or solvate thereof, preferably in the form of a pharmaceutical composition, which when dosed in divided doses (also known as split doses) produces a greater anti-tumour effect than when a single dose is given.

Anti-tumour effects include but are not limited to, inhibition of tumour growth, tumour growth delay, regression of tumour, shrinkage of tumour, increased time to re-growth of tumour on cessation of treatment, slowing of disease progression. It is expected that when a compound of the present invention is administered to a warm-blooded animal such as a human, in need of treatment for cancer involving a solid tumour, said method of treatment will produce an effect, as measured by, for example, one or more of: the extent of the anti-tumour effect, the response rate, the time to disease progression and the survival rate.

According to a further aspect of the fifth feature of the present invention there is provided a method for the production of a vascular damaging effect in a warm-blooded animal such as a human, which comprises administering to said animal in divided doses an effective amount of a compound of Formula (I), Formula (II) or Formula (IIa), or pharmaceutically-acceptable salt, pro-drug or solvate thereof, preferably in the form of a pharmaceutical composition.

According to a further aspect of the fifth feature of the present invention there is provided a method for the treatment of a cancer involving a solid tumour in a warm-blooded animal such as a human, which comprises administering to said animal in divided doses an effective amount of a compound of Formula (I), Formula (II) or Formula (IIa), or pharmaceutically-acceptable salt, pro-drug or solvate thereof, preferably in the form of a pharmaceutical composition.

According to a further aspect of the fifth feature of the present invention there is provided a medicament comprising two or more fractions of doses of a compound of Formula (I), Formula (II) or Formula (IIa), or pharmaceutically-acceptable salt, pro-drug or solvate thereof, preferably in the form of a pharmaceutical composition, which together add up to a total daily dose, for administration in divided doses for use in a method of treatment of a human or animal body by therapy.

According to a further aspect of the fifth feature of the present invention there is provided a kit comprising two or more fractions of doses of a compound of Formula (I), Formula (II) or Formula (IIa), or pharmaceutically-acceptable salt, pro-drug or solvate thereof, preferably in the form of a pharmaceutical composition, which together add up to a total daily dose, for administration in divided doses.

According to a further aspect of the fifth feature of the present invention there is provided a kit comprising:

a) two or more fractions of doses of a compound of Formula (I), Formula (II) or Formula (IIa), or pharmaceutically-acceptable salt, pro-drug or solvate thereof, which together add up to a total daily dose, in unit dosage forms for administration in divided doses; and b) container means for containing said dosage forms.

According to a further aspect of the fifth feature of the present invention there is provided a kit comprising a) two or more fractions of doses of a compound of Formula (I), Formula (II) or Formula (IIa), or pharmaceutically-acceptable salt, pro-drug or solvate thereof, which together add up to a total daily dose, together with an excipient or carrier, in unit dosage forms; and b) container means for containing said dosage forms.

According to a further aspect of the fifth feature of the present invention there is provided the use of a compound of Formula (I), Formula (II) or Formula (IIa), or pharmaceutically-acceptable salt, pro-drug or solvate thereof, in the manufacture of a medicament for administration in divided doses for use in the production of a vascular damaging effect in a warm-blooded animal such as a human.

According to a further aspect of the fifth feature of the present invention there is provided the use of a compound of Formula (I), Formula (II) or Formula (IIa), or pharmaceutically-acceptable salt, pro-drug or solvate thereof, in the manufacture of a medicament for administration in divided doses for use in the production of an anti-cancer effect in a warm-blooded animal such as a human.

According to a further aspect of the fifth feature of the present invention there is provided the use of a compound of Formula (I), Formula (II) or Formula (IIa), or pharmaceutically-acceptable salt, pro-drug or solvate thereof, in the manufacture of a medicament for administration in divided doses for use in the production of an anti-tumour effect in a warm-blooded animal such as a human.

Divided doses, also called split doses, means that the total dose to be administered to a warm-blooded animal, such as a human, in any one day period (for example one 24 hour period from midnight to midnight) is divided up into two or more fractions of the total dose and these fractions are administered with a time period between each fraction of about greater than 0 hours to about 10 hours, preferably about 1 hour to about 6 hours, more preferably about 2 hours to about 4 hours. The fractions of total dose may be about equal or unequal.

Preferably the total dose is divided into two parts which may be about equal or unequal.

The time intervals between doses may be for example selected from: about 1 hour, about 1.5 hours, about 2 hours, about 2.5 hours, about 3 hours, about 3.5 hours, about 4 hours, about 4.5 hours, about 5 hours, about 5.5 hours and about 6 hours.

The time intervals between doses may be any number (including non-integers) of minutes between greater than 0 minutes and 600 minutes, preferably between 45 and 375 minutes inclusive. If more than two doses are administered the time intervals between each dose may be about equal or unequal.

Preferably two doses are given with a time interval in between them of greater than or equal to 1 hour and less than 6 hours.

More preferably two doses are given with a time interval in between them of greater than or equal to two hours and less than 5 hours.

Yet more preferably two doses are given with a time interval in between them of greater than or equal to two hours and less than or equal to 4 hours.

Particularly the total dose is divided into two parts which may be about equal or unequal with a time interval between doses of greater than or equal to about two hours and less than or equal to about 4 hours.

More particularly the total dose is divided into two parts which may be about equal with a time interval between doses of greater than or equal to about two hours and less than or equal to about 4 hours.

For the avoidance of doubt the term 'about' in the description of time periods means the time given plus or minus 15 minutes, thus for example about 1 hours means 45 to 75 minutes, about 1.5 hours means 75 to 105 minutes. Elsewhere the term 'about' has its usual dictionary meaning.

Although the compounds of the Formula (I), Formula (II) or Formula (IIa) are primarily of value as therapeutic agents for use in warm-blooded animals (including man), they are also useful whenever it is required to inhibit and/or reverse and/or alleviate symptoms of angiogenesis and/or any disease state associated with angiogenesis. Thus, they are useful as pharmacological tools for use in the development of new biological tests and in the search for new pharmacological agents.

Biological Assay

Colchicine Binding Site Competitive Assay Kit

The ability of a ligand to bind specifically to the colchicine binding site on tubulin, an indicator of the vascular damaging activity, was assessed using a size exclusion chromatography assay kit from "Cytoskeleton" (1650 Fillmore St. #240, Denver, Colo. 80206, U.S.A.) Catalogue number of kit: BK023.

The following reagents were used:

tubulin buffer, to give 0.1 mM GTP, 0.5 mM $MgCl_2$, 0.5 mM EGTA, 40 mM PIPES buffer at pH 6.9 in the final reaction mix;

purified tubulin protein from bovine brain at 1 mg/ml in tubulin buffer;

0.02 mM fluorescent colchicine in tubulin buffer [FITC (fluorescein isothiocyanate)-labelled];

2 mM colchicine in tubulin buffer;

0.2 mM vinblastine in tubulin buffer; and

G-25 Sephadex™ Fine—particle size 34–138 $\mu$m.

The reaction was performed as follows:

8 $\mu$l of test compound (dissolved in DMSO) was gently mixed with 150 $\mu$l of tubulin. This was then incubated at 37° C. for 30 minutes. Then 4 $\mu$l of the fluorescent colchicine was added, the incubation mix vortexed for 5 seconds and then incubated for a further 30 minutes at 37° C.

At the end of the reaction incubation size exclusion chromatography was performed to separate the tubulin with fluorescent colchicine bound from the free, unbound colchicine. If a test compound inhibited fluorescent colchicine binding then a reduced signal is measured and the compound is confirmed as a colchicine site binding moiety.

Size exclusion chromatography was performed as follows, using chromatography columns filled with 3 mls of G-25 Sephadex™ Fine slurry. The incubation mixture was pipetted onto the column fractions was detected on a spectrophotometer which excites at 485 nm and emits at 535 nm.

Control incubations were also performed, 8 μl DMSO (negative control) and 8 μl colchicine stock (positive competition control), instead of the 8 μl of test compound in the incubation mixture.

The degree of competition of colchicine binding by either unlabelled colchicine or test compound was calculated relative to the DMSO negative control.

Compounds of Formula (I), Formula (II) or Formula (IIa) encompass vascular damaging agents and pro-drugs of vascular damaging agents. Pro-drugs of vascular damaging agents are believed to be cleaved in-vivo. Without being bound by theoretical considerations these pro-drugs may have lower activity in the in-vitro colchicine binding site competitive assay, than would be anticipated when the activity of these compounds is measured in cell based assays or in-vivo.

The invention will now be illustrated with the following non-limiting Examples in which, unless otherwise stated:

(i) evaporations were carried out by rotary evaporation in vacuo and work-up procedures were carried out after removal of residual solids such as drying agents by filtration;

(ii) operations were carried out at ambient temperature, that is in the range 18–25° C. and under an atmosphere of an inert gas such as argon or nitrogen;

(iii) yields are given for illustration only and are not necessarily the maximum attainable;

(iv) the structures of the end-products of the Formula (I), Formula (II) or Formula (IIa) were confirmed by nuclear (generally proton) magnetic resonance (NMR) and mass spectral techniques; proton magnetic resonance chemical shift values were measured on the delta scale and peak multiplicities are shown as follows: s, singlet; d, doublet; t, triplet; m, multiplet; br, broad; q, quartet, quin, quintet;

(v) intermediates were not generally fully characterised and purity was assessed by thin layer chromatography (TLC), high-performance liquid chromatography (HPLC), infra-red (IR) or NMR analysis;

(vi) flash chromatography was performed on silica (Merck Keiselgel: Art 9385);

(vii) OASIS™ is a macroporous co-polymer, used to purify hydrophilic compounds, made from a balanced ratio of lipophilic divinylbenzene and hydrophilic N-vinylpyrrolidone. OASIS™ is described in the following patents, U.S. Pat. No. 5,882,521, U.S. Pat. No. 5,976,376 and U.S. Pat. No. 6,106,721. OASIS™ sample extraction products were obtained from Waters Corporation (Milford, Mass., USA).

| Abbreviations | |
|---|---|
| 4-Dimethylaminopyridine | DMAP |
| 1-(3-Dimethylaminopropyl)-3-ethylcarbodiimide hydrochloride | EDCI |
| Dimethyl sulphoxide | DMSO |
| N-(9-fluorenylmethoxycarbonyl) | N-FMOC |

EXAMPLE 1

7-(4-Methoxyphenoxy)-2H-1,4-benzoxazin-3(4H)-one

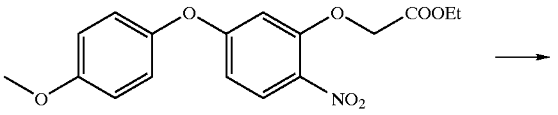

1

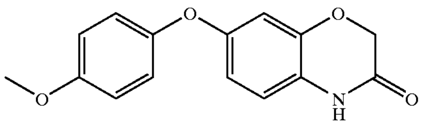

Example 1

A solution of 1 (1.2 g; 3.4 mmol) in AcOH (22 ml) and water (3 ml) was treated portionwise with zinc (2.3 g; 34 mmol). The mixture was stirred at room temperature for 1 hour. After evaporation to dryness the residue was taken up in EtOAc, filtered and the solid washed well with EtOAc. The filtrate was washed with water, then brine and dried over $MgSO_4$. The residue was purified by flash chromatography eluting with increasingly polar mixtures of EtOAc/hexanes (40 to 50% EtOAc) to give 7-(4-methoxyphenoxy)-2H-1,4-benzoxazin-3(4H)-one as a beige solid (0.71 g).

Yield: 76%

M. Pt. 163–164° C.

$^1$H NMR spectrum (DMSO $d_6$): 3.74 (s, 3H); 4.55 (s, 2H); 6.54 (m, 2H); 6.85 (d, 1H); 6.95 (m, 4H); 10.65 (br s, 1H).

LCMS-ESI: 272 $[MH]^+$

| | | | | |
|---|---|---|---|---|
| Elemental analysis: | Found | C 66.66 | H 4.8 | N 5.24 |
| $C_{15}H_{11}N_3OS$ | Requires | C 66.41 | H 4.83 | N 5.16 |

The starting material was prepared as follows:

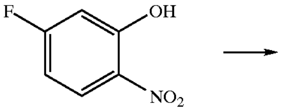

2

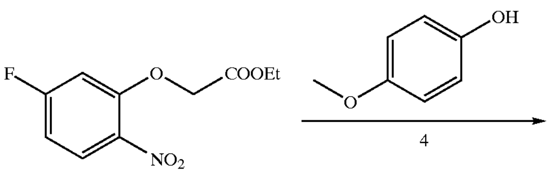

4

3

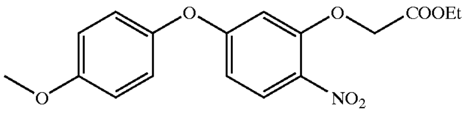

1

A solution of 2 (31.4 g; 200 mmol) in acetone (300 ml) was treated with $K_2CO_3$ (33 g; 240 mmol) and warmed to 40° C. A solution of ethyl bromoacetate (35 g; 210 mmol) in acetone (30 ml) was added over 5 minutes and the mixture was stirred and heated at 70° C. for 2 hour 30 minutes and allowed to cool. The mixture was evaporated to dryness, taken up in $Et_2O$ and the organic phase washed with water, brine and dried over $MgSO_4$. Evaporation and trituration with hexanes gave 3 as a pale yellow solid (47.0 g).

Yield: 97%

$^1H$ NMR spectrum ($CDCl_3$): 1.30 (t, 3H); 4.29 (q, 2H); 4.77 (s, 2H); 6.69 (dd, 1H); 6.81 (ddd, 1H); 7.98 (dd, 1H).

LCMS-ESI: 244 $[M]^+$

Compound 4 (1.24 g; 10 mmol) was dissolved in N,N-dimethylacetamide (10 ml) under argon and was treated with NaH (450 mg; 60% in oil; 11 mmol). The mixture was stirred for 1 hour and a solution of compound 3 (2.43 g; 10 mmol) was added. The mixture was heated at 60° C. and stirred for 20 hours and then allowed to cool. The mixture was poured into water and extracted with EtOAc (3×). The organic phase was washed with water, saturated, aqueous. $NaHCO_3$, then brine and dried over $MgSO_4$.

The residue (3 g) was purified by flash chromatography eluting with increasingly polar mixtures of EtOAc/hexanes (20 to 30% EtOAc). The appropriate fractions were evaporated to give 1 as a yellow oil (2.9 g).

Yield: 84%

$^1H$ NMR spectrum ($CDCl_3$): 1.28 (t, 3H); 3.83 (s, 3H); 4.24 (q, 2H); 4.69 (s, 2H); 6.46 (d, 1H); 6.51 (dd, 1H); 6.97 (m, 4H); 7.94 (d, 1H).

LCMS-ESI: 348 $[MH]^+$

EXAMPLE 2

7-(4-Hydroxyphenoxy)-2H-1,4-benzoxazin-3(4H)-one

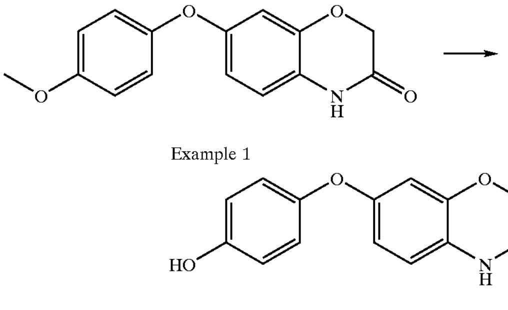

Example 1

Example 2

A solution of 7-(4-methoxyphenoxy)-2H-1,4-benzoxazin-3(4H)-one (120 mg; 0.44 mmol) in $CH_2Cl_2$ (1 ml) was treated with $BBr_3$ (332 mg; 1.33 mmol). The mixture was stirred at room temperature for 3 hours. After evaporation to dryness the residue was taken up in EtOAc and water. The organic phase was washed with brine and dried over $MgSO_4$. The residue (110 mg) was triturated with EtOAc, filtered and dried to give 7-(4-hydroxyphenoxy)-2H-1,4-benzoxazin-3(4H)-one as a biege solid (85 mg), Melting point 250–251° C.

Yield: 75%

$^1H$ NMR spectrum (DMSO $d_6$): 4.54 (s, 2H); 6.51 (m, 2H); 6.75 (d, 2H); 6.84 (m, 3H); 9.31 (s, 1H); 10.62 (s, 1H).

LCMS-ESI: 258 $[MH]^+$

| | | | | |
|---|---|---|---|---|
| Elemental analysis: | Found | C 64.74 | H 4.51 | N 5.29 |
| $C_{14}H_{11}NO_4$; 0.1 $H_2O$ | Requires | C 64.91 | H 4.36 | N 5.41 |

EXAMPLE 3

7-[(4-Aminophenyl)sulfanyl]-2H-1,4-benzoxazin-3(4H)-one

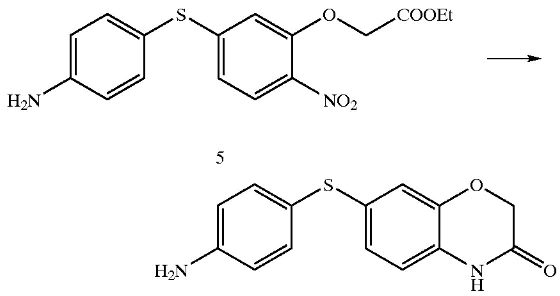

5

Example 3

Using the general method described for Example 1, 7-[(4-aminophenyl)sulfanyl]-2H-1,4-benzoxazin-3(4H)-one was obtained from 5 (2.0 g; 5.7 mmol) after purification by flash chromatography eluting with increasingly polar mixtures of EtOAc/hexanes (70 to 100% EtOAc). The product was a beige solid (1.41 g), Melting point 232–234° C.

Yield: 90%

$^1H$ NMR spectrum (DMSO $d_6$): 4.51 (s, 2H); 5.48 (s, 2H); 6.58 (m, 3H); 6.70 (dd, 1H); 6.79 (d, 1H); 7.14 (m, 2H); 10.66 (s, 1H).

LCMS-ESI: 271 $[M-H]^-$

| | | | | | |
|---|---|---|---|---|---|
| Elemental analysis: | Found | C 61.90 | H 4.44 | N 10.29 | S 11.29 |
| $C_{14}H_{12}N_2O_2S$ | Requires | C 61.75 | H 4.44 | N 10.29 | S 11.77 |

The starting material was prepared as follows:

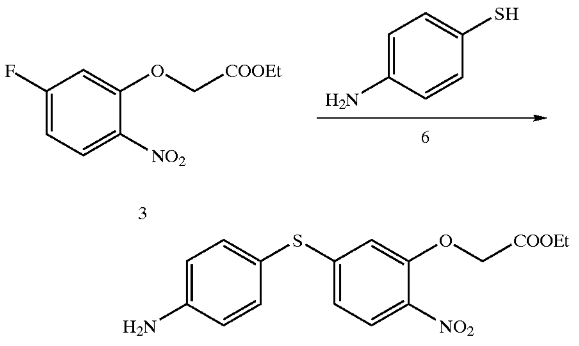

6

3

5

Compound 3 (2.43 g; 10 mmol) and compound 6 (1.25 g; 10 mmol) were dissolved in N-methyl-2-pyrrolidinone (20 ml) under argon and were treated with $K_2CO_3$ (2.1 g; 15 mmol). The mixture was heated at 80° C. and stirred for 2.5 hours and then allowed to cool. The mixture was poured into water and extracted with EtOAc (3×). The organic phase was washed with water, brine and dried over $MgSO_4$.

The residue (3.6 g) was purified flash chromatography eluting with increasingly polar mixtures of EtOAc/hexanes (40 to 50% EtOAc). The appropriate fractions were evaporated to give 5 as a pale beige solid (2.1 g), Melting point 110–111° C.

Yield: 60%

$^1$H NMR spectrum ($CDCl_3$): 1.28 (t, 3H); 3.97 (s, 2H); 4.22 (q, 2H); 4.62 (s, 2H); 6.53 (d, 1H); 6.67 (dd, 1H); 6.72 (m, 2H); 7.30 (m, 2H); 7.78 (d, 1H).

LCMS-ESI: 349 $[MH]^+$

| | | | | | |
|---|---|---|---|---|---|
| Elemental analysis: | Found | C 55.5 | H 4.67 | N 8.16 | S 8.41 |
| $C_{16}H_{16}N_2O_5S$ | Requires | C 55.16 | H 4.63 | N 8.04 | S 9.2 |

EXAMPLE 4

7-[(2-Aminophenyl)sulfanyl]-2H-1,4-benzoxazin-3(4H)-one

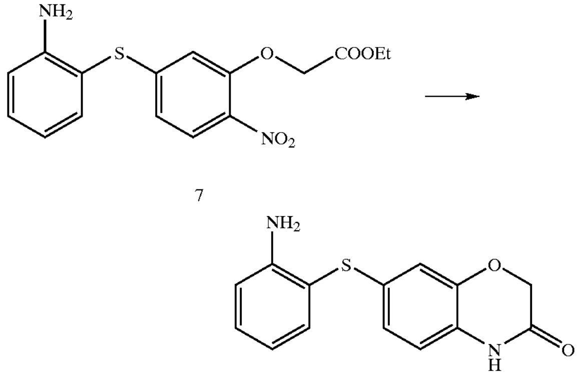

7

Example 4

Using the general method described for Example 1, 7-[(2-aminophenyl)sulfanyl]-2H-1,4-benzoxazin-3(4H)-one was obtained from 7 (3.5 g; 10 mmol) after purification by flash chromatography eluting with increasingly polar mixtures of EtOAc/hexanes (40 to 50% EtOAc). The product was a white solid (1.05 g), Melting point 204–205° C.

Yield: 39%

$^1$H NMR spectrum (DMSO $d_6$): 4.54 (s, 2H); 5.38 (s, 2H); 6.59 (t, 1H); 6.64 (d, 1H); 6.8 (m, 3H); 7.17 (t, 1H); 7.3 (dd, 1H); 10.7 (s, 1H).

LCMS-ESI: 271 $[M-H]^-$

| | | | | | |
|---|---|---|---|---|---|
| Elemental analysis: | Found | C 62.20 | H 4.51 | N 10.32 | S 11.35 |
| $C_{14}H_{12}N_2O_2S$ | Requires | C 61.75 | H 4.44 | N 10.29 | S 11.77 |

The starting material was prepared as follows:

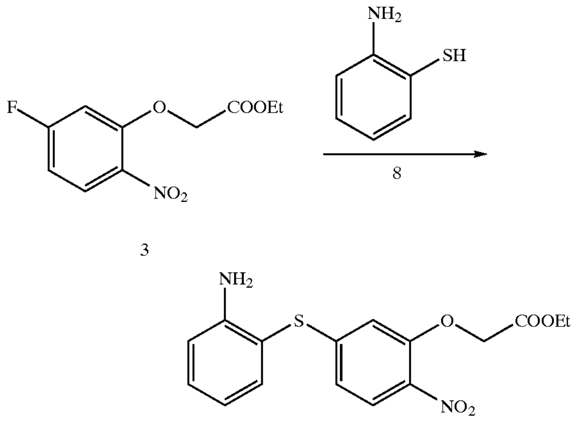

3

8

7

Using the general method described for the starting material in Example 3, except that the mixture was heated for 3 hours, 7 was obtained from 3 (2.43 g; 10 mmol) and 8 (1.25 g; 10 mmol) after purification by flash chromatography eluting with increasingly polar mixtures of EtOAc/hexanes (20 to 25% EtOAc). The appropriate fractions were evaporated to give 7 as a pale yellow solid (3.7 g), Melting point 70–71° C.

Yield: 100%

$^1$H NMR spectrum ($CDCl_3$): 1.27 (t, 3H); 4.20 (q, 2H); 4.28 (s, 2H); 4.61 (s, 2H); 6.51 (d, 1H); 6.71 (dd, 1H); 6.79 (dt, 1H); 6.83 (dd, 1H); 7.31 (dt, 1H); 7.41 (dd, 1H); 7.81 (d, 1H).

LCMS-ESI: 349 $[MH]^+$

| | | | | | |
|---|---|---|---|---|---|
| Elemental analysis: | Found | C 55.42 | H 4.76 | N 8.15 | S 8.36 |
| $C_{16}H_{16}N_2O_5S$ | Requires | C 55.16 | H 4.63 | N 8.04 | S 9.2 |

EXAMPLE 5

7-[(3-Aminophenyl)sulfanyl]-2H-1,4-benzoxazine-3(4H)-one

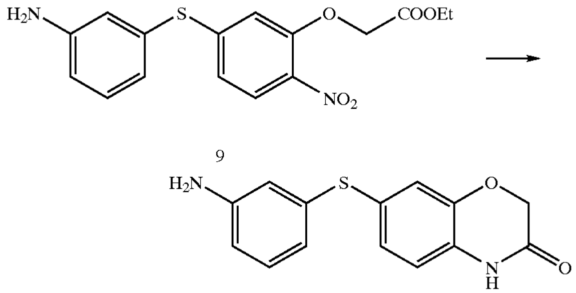

9

Example 5

Using the general method described for Example 1, 7-[(3-aminophenyl)sulfanyl]-2H-1,4-benzoxazin-3(4H)-one was obtained from 9 (8.65 g; 25 mmol) after purification by flash chromatography eluting with increasingly polar mixtures of EtOAc/hexanes (50 to 70% EtOAc). The product was a beige solid (3.05 g), Melting point 181–182° C.

Yield: 45%

$^1H$ NMR spectrum (DMSO $d_6$): 4.59 (s, 2H); 5.22 (s, 2H); 6.41 (m, 1H); 6.5 (m, 2H); 6.9 (m, 2H); 7.0 (m, 2H); 10.82 (s, 1H).

LCMS-ESI: 271 $[M-H]^-$

| | | | | | |
|---|---|---|---|---|---|
| Elemental analysis: | Found | C 61.87 | H 4.51 | N 10.13 | S 11.52 |
| $C_{14}H_{12}N_2O_2S$ | Requires | C 61.75 | H 4.44 | N 10.29 | S 11.77 |

The starting material was prepared as follows:

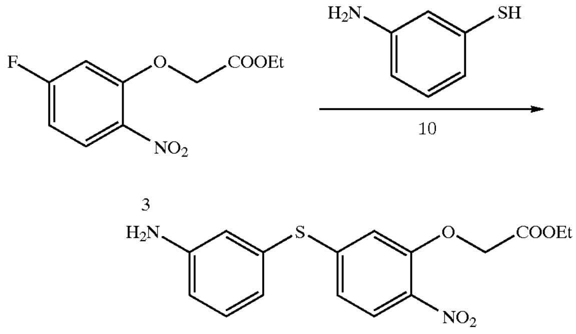

3

10

9

Using the general method described for the starting material in Example 3, except that the mixture was heated for 3 hours, 9 was obtained from 3 (9.72 g; 40 mmol) and 10 (5.0 g; 40 mmol) after purification by flash chromatography eluting with increasingly polar mixtures of EtOAc/hexanes (30 to 50% EtOAc). The appropriate fractions were evaporated to give 9 as a yellow oil (13.78 g).

Yield: 99%

$^1H$ NMR spectrum ($CDCl_3$): 1.27 (t, 3H); 3.81 (s, 2H); 4.22 (q, 2H); 4.64 (s, 2H); 6.67 (d, 1H); 6.72 (m, 1H); 6.79 (m, 2H); 6.86 (m, 1H); 7.20 (t, 1H); 7.8 (d, 1H).

LCMS-ESI: 349 $[MH]^+$

| | | | | | |
|---|---|---|---|---|---|
| Elemental analysis: | Found | C 55.36 | H 4.78 | N 7.83 | S 8.76 |
| $C_{16}H_{16}N_2O_5S$ | Requires | C 55.16 | H 4.63 | N 8.04 | S 9.2 |

EXAMPLE 6

7-[(4-Hydroxyphenyl)sulfanyl]-2H-1,4-benzoxazin-3(4H)-one

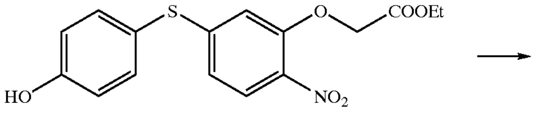

11

-continued

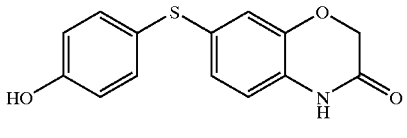

Example 6

Using the general method described for Example 1, 7-[(4-Hydroxyphenyl)sulfanyl]-2H-1,4-benzoxazin-3(4H)-one was obtained from 11 (1.9 g; 5.4 mmol) after purification by flash chromatography eluting with increasingly polar mixtures of EtOAc/hexanes (50 to 70% EtOAc). The product was a beige solid (1.32 g), Melting point 224–225° C.

Yield: 89%

$^1H$ NMR spectrum (DMSO $d_6$): 4.54 (s, 2H); 6.67 (d, 1H); 6.8 (m, 4H); 7.27 (d, 2H); 9.82 (br s, 1H); 10.71 (s, 1H).

LCMS-ESI: 272 $[M-H]^-$

| | | | | | |
|---|---|---|---|---|---|
| Elemental analysis: | Found | C 61.53 | H 4.17 | N 5.18 | S 11.03 |
| $C_{14}H_{11}NO_3S$ | Requires | C 61.53 | H 4.06 | N 5.12 | S 11.73 |

The starting material was prepared as follows:

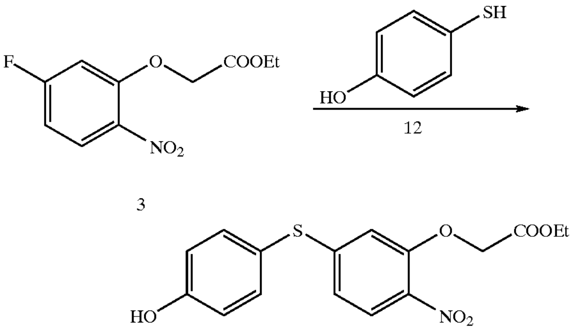

3

12

11

Using the general method described for the starting material in Example 3, 11 was obtained from 3 (2.43 g; 10 mmol) and 12 (1.26 g; 10 mmol) after purification by flash chromatography eluting with increasingly polar mixtures of EtOAc/hexanes (30 to 50% EtOAc). The appropriate fractions were evaporated to give 11 as a pale yellow solid (2.48 g), Melting point 156–157° C. Yield: 71% $^1H$ NMR spectrum ($CDCl_3$): 1.28 (t, 3H); 4.21 (q, 2H); 4.61 (s, 2H); 6.50 (d, 1H); 6.68 (dd, 1H); 6.94 (d, 2H); 7.36 (d, 2H); 7.78 (d, 1H); 9.28 (s, 1H). LCMS-ESI: 348 $[M-H]^-$

| | | | | | |
|---|---|---|---|---|---|
| Elemental analysis: | Found | C 55.12 | H 4.45 | N 4.07 | S 8.82 |
| $C_{16}H_{15}NO_6S$ | Requires | C 55.01 | H 4.33 | N 4.01 | S 9.18 |

EXAMPLE 7

7-[(3,4-Dimethoxyphenyl)sulfanyl]-2H-1,4-benzoxazin-3(4H)-one

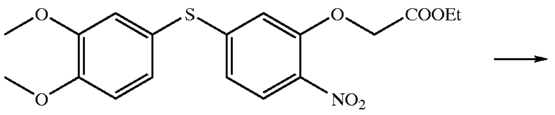

13

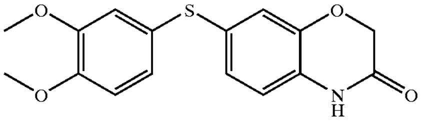

Example 7

Using the general method described for Example 1,7-[(3,4-dimethoxyphenyl)sulfanyl]-2H-1,4-benzoxazin-3(4H)-one was obtained from 13 (3.34 g; 8.5 mmol) after purification by flash chromatography eluting with increasingly polar mixtures of EtOAc/hexanes (50 to 70% EtOAc). The product was a pink solid (1.95 g). A small quantity was recrystallised from EtOAc, Melting point 170–171° C. Yield: 73% $^1$H NMR spectrum (DMSO $d_6$): 3.75 (s, 3H), 3.78 (s, 3H); 4.57 (s, 2H); 6.78 (d, 1H); 6.87 (m, 2H); 7.0 (m, 3H); 10.76 (s, 1H). LCMS-ESI: 316 $[M-H]^-$

| | | | | | |
|---|---|---|---|---|---|
| Elemental analysis: | Found | C 60.18 | H 4.94 | N 4.34 | S 9.23 |
| $C_{16}H_{15}NO_4S$ | Requires | C 60.55 | H 4.76 | N 4.41 | S 10.10 |

The starting material was prepared as follows:

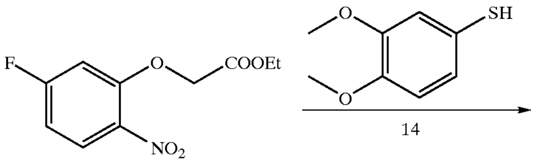

3

14

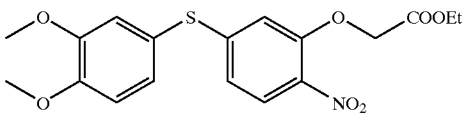

13

Using the general method described for the starting material in Example 3, 13 was obtained from 3 (2.43 g; 10 mmol) and 14 (1.7 g; 10 mmol) after purification by flash chromatography eluting with increasingly polar mixtures of EtOAc/hexanes (30 to 50% EtOAc). The appropriate fractions were evaporated to give 13 as a yellow solid (3.34 g), Melting Point 97–98° C. Yield: 85% $^1$H NMR spectrum ($CDCl_3$): 1.27 (t, 3H); 3.88 (s, 3H); 3.94 (s, 3H); 4.20 (q, 2H); 4.62 (s, 2H); 6.55 (d, 1H); 6.70 (dd, 1H); 6.94 (d, 1H); 7.0 (d, 1H); 7.15 (dd, 1H); 7.80 (d, 1H). LCMS-ESI: 394 $[MH]^+$

| | | | | | |
|---|---|---|---|---|---|
| Elemental analysis: | Found | C 55.17 | H 4.92 | N 3.58 | S 7.09 |
| $C_{18}H_{19}NO_7S$ | Requires | C 54.95 | H 4.87 | N 3.56 | S 8.15 |

EXAMPLE 8

7-[(3,4-Dihydroxyphenyl)sulfanyl]-2H-1,4-benzoxazin-3(4H)-one

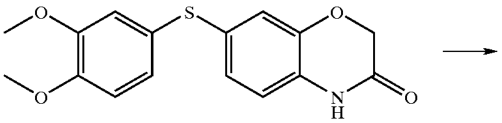

Example 7

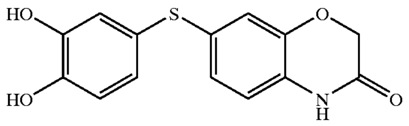

Example 8

A solution of Example 7 (7-[(3,4-dimethoxyphenyl)sulfanyl]-2H-1,4-benzoxazin-3(4H)-one)(320 mg; 1.0 mmol) in $CH_2Cl_2$ (2 ml) was treated with $BBr_3$ (750 mg; 3.0 mmol). The mixture was stirred at room temperature for 3 hours. After evaporation to dryness the residue was taken up in EtOAc and water. The organic phase was washed with water, brine and dried over MgSO4. The residue (110 mg) was triturated with EtOAc/$CH_2Cl_2$, filtered and dried to give 7-[(3,4-dihydroxyphenyl)sulfanyl]-2H-1,4-benzoxazin-3(4H)-one as a beige solid (280 mg), Melting point 236–238° C. Yield: 96% $^1$H NMR spectrum (DMSO $d_6$): 4.54(s, 2H); 6.69 (d, 1H); 6.74–6.84 (m, 5H); 9.22 (s, 1H); 9.27 (s, 1H); 10.72 (s, 1H). LCMS-ESI: 288 $[M-H]^-$

| | | | | | |
|---|---|---|---|---|---|
| Elemental analysis: | Found | C 57.98 | H 4.10 | N 4.63 | S 10.77 |
| $C_{14}H_{11}NO_4S$ | Requires | C 58.12 | H 3.83 | N 4.84 | S 11.08 |

EXAMPLE 9

7-Benzylsulfanyl-2H-1,4-benzoxazin-3(4H)-one

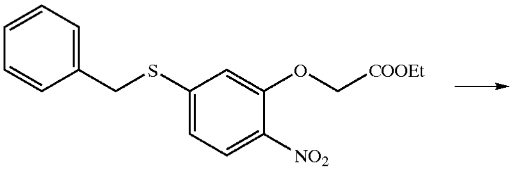

15

-continued

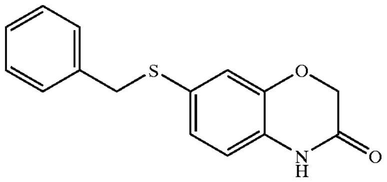

Example 9

Using the general method described for Example 1, 7-benzylsulfanyl-2H-1,4-benzoxazin-3-(4H)-one was obtained from 15 (1.5 g, 4.3 mmol) after purification by flash chromatography eluting with increasingly polar mixtures of EtOAc/hexanes (30 to 50% EtOAc). The product was a beige solid (1.11 g), Melting point 154–155° C. Yield: 95% $^{1}H$ NMR spectrum (DMSO $d_6$): 4.15 (s, 2H); 4.55 (s, 2H); 6.80 (d, 1H); 6.92 (m, 2H); 7.21–7.32 (m, 5H); 10.71 (s, 1H). LCMS-ESI: 270 $[M-H]^-$

| | | | | | |
|---|---|---|---|---|---|
| Elemental analysis: | Found | C 66.15 | H 4.86 | N 5.27 | S 10.34 |
| $C_{15}H_{13}NO_2S$ | Requires | C 66.40 | H 4.83 | N 5.16 | S 11.82 |

The starting material was prepared as follows:

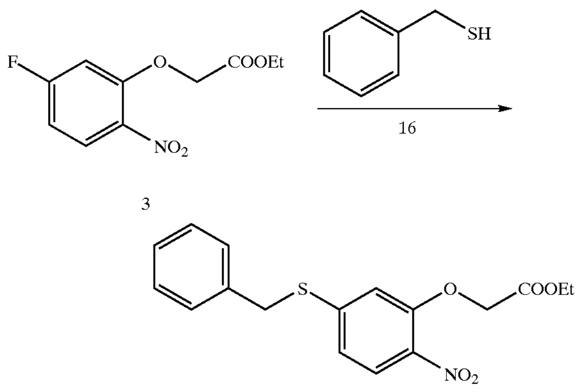

3 16 15

Compounds 3 (1.215 g; 5 mmol) and 16 (0.62 g; 5 mmol) were dissolved in DMF (5 ml) and treated with triethylamine (0.85 ml; 6 mmol). The mixture was stirred and heated at 70° C. for 3 days and then allowed to cool. The mixture was poured into EtOAc and the organic phase washed with aqueous NaOH (1N), water than brine and dried over $MgSO_4$. Evaporation gave essentially pure 15 (1.69 g). A small quantity was purified by flash chromatography eluting with increasingly polar mixtures of EtOAc/hexanes (20 to 40% EtOAc). The appropriate fractions were evaporated to give a yellow solid, Melting point 76–77° C. Yield: 99% $^{1}H$ NMR spectrum ($CDCl_3$): 1.29 (t, 3H); 4.20 (s, 2H); 4.26 (q, 2H); 4.65 (s, 2H); 6.77 (d, 1H); 6.93 (dd, 1H); 7.35 (m, 5H); 7.83 (d, 1H). LCMS-ESI: 348 $[MH]^+$

| | | | | | |
|---|---|---|---|---|---|
| Elemental analysis: | Found | C 58.06 | H 4.89 | N 4.15 | S 7.22 |
| $C_{17}H_{17}NO_5S$, 0.2 $H_2O$ | Requires | C 58.17 | H 5.00 | N 3.99 | S 9.14 |

EXAMPLE 10

7-(4-Chlorobenzylsufanyl)-2H-1,4-benzoxazin-3(4H)-one

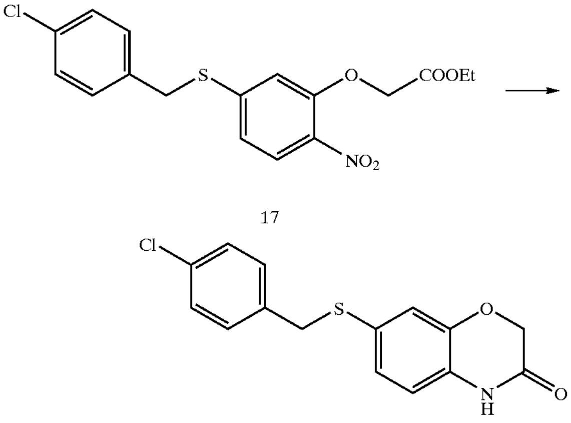

17

Example 10

Using the general method described in Example 1, 7-(4-chloro-benzylsulfanyl)-2H-1,4-benzoxazin-3(4H)-one was obtained from 17 (1.7 g; 4.4 mmol) after purification by flash chromatography eluting with increasingly polar mixtures of EtOAc/hexanes (30 to 50% EtOAc). The product was a cream solid (1.04 g), Melting point 174–175° C. Yield; 76% $^{1}H$ NMR spectrum (DMSO $d_6$): 4.15 (s, 2H); 4.55 (s, 2H); 6.79 (d, 1H); 6.90 (dd, 1H); 6.93 (d, 1H); 7.32 (m, 4H); 10.72 (s, 1H). LCMS-ESI: 304.5 $[M-H]^-$

| | | | | | |
|---|---|---|---|---|---|
| Elemental analysis: | Found | C 58.93 | H 4.05 | N 4.67 | S 9.90 |
| $C_{15}H_{12}ClNO_2S$ | Requires | C 58.92 | H 3.96 | N 4.58 | S 10.49 |

The starting material was prepared as follows:

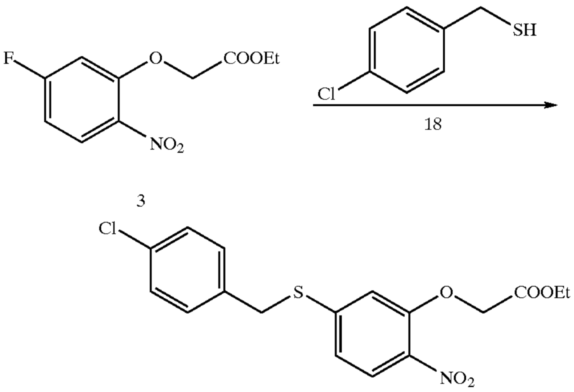

18 3 17

Using the general method described for the starting material in Example 9, 17 (1.89 g) was obtained from 3 (1.215 g; 5 mmol) and 18 (0.79 g; 5 mmol). A small quantity was purified by flash chromatography eluting with increasingly polar mixtures of EtOAc/hexanes (30 to 50% EtOAc). The appropriate fractions were evaporated to give 17 as yellow solid, Melting point 97–98° C. Yield: 99% $^1$H NMR spectrum ($CDCl_3$): 1.30 (t, 3H); 4.16 (s, 2H); 4.27 (q, 2H); 4.68 (s, 2H); 6.78 (d, 1H); 6.93 (dd, 1H); 7.31 (m, 4H); 7.85 (d, 1H). LCMS-ESI: 382.5 $[MH]^+$

| | | | | | |
|---|---|---|---|---|---|
| Elemental analysis: | Found | C 53.25 | H 4.29 | N 3.77 | S 7.29 |
| $C_{17}H_{16}ClNO_5S$ | Requires | C 53.48 | H 4.22 | N 3.67 | S 8.40 |

EXAMPLE 11

7-(4-tert-Butylbenzylsulfanyl)-2H-1,4-benzoxazin-3(4)-one

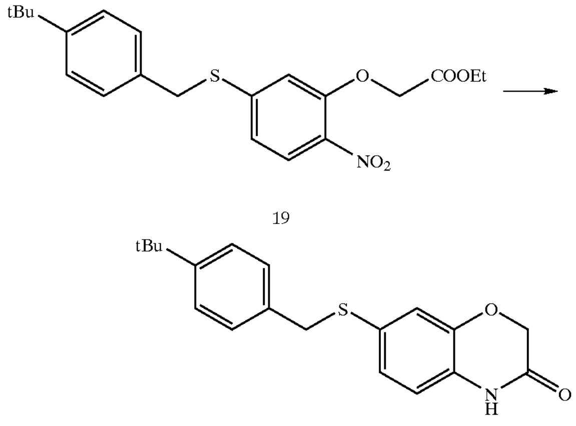

19

Example 11

Using the general method described in Example 1, 7-(4-tert-butyl-benzylsulfanyl)-2H-1,4-benzoxazin-3(4)-one was obtained from 19 (1.8 g; 4.4 mmol) after purification by flash chromatography eluting with increasingly polar mixtures of EtOAc/hexanes (30 to 50% EtOAc). The product was a beige solid (1.23 g), Melting point 134–136° C. Yield: 84% $^1$H NMR spectrum (DMSO $d_6$): 1.25 (s, 9H); 4.13 (s, 2H); 4.55 (s, 2H); 6.80 (d, 1H); 6.93 (m, 2H); 7.29 (m, 4H); 10.71 (s, 1H). LCMS-ESI: 326 $[M-H]^-$

| | | | | | |
|---|---|---|---|---|---|
| Elemental analysis: | Found | C 69.55 | H 6.57 | N 4.31 | S 8.79 |
| $C_{19}H_{21}NO_2S$ | Requires | C 69.69 | H 6.46 | N 4.28 | S 9.79 |

The starting material was prepared as follows:

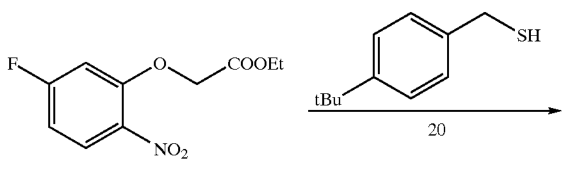

20

3

-continued

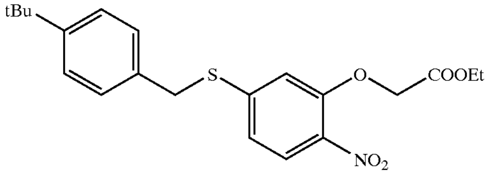

19

Using the general method described for the starting material in Example 9, 19 (2.0 g) was obtained from 3 (1.215 g; 5 mmol) and 18 (0.9 g; 5 mmol). A small quantity was purified by flash chromatography eluting with increasingly polar mixtures of EtOAc/hexanes (30 to 50% EtOAc). The appropriate fractions were evaporated to give 19 as a yellow solid, Melting point 98–99° C. Yield: 99% $^1$H NMR spectrum ($CDCl_3$): 1.27 (t, 3H); 1.31 (s, 9H); 4.17 (s, 2H); 4.26 (q, 2H); 4.64 (s, 2H); 6.77 (d, 1H); 6.94 (dd, 1H); 7.33 (m, 4H); 7.84 (d, 1H). LCMS-ESI: 404 $[MH]^+$

| | | | | | |
|---|---|---|---|---|---|
| Elemental analysis: | Found | C 62.65 | H 6.36 | N 3.75 | S 6.71 |
| $C_{21}H_{25}NO_5S$ | Requires | C 62.51 | H 6.25 | N 3.47 | S 7.95 |

EXAMPLE 12

7-(4-Methoxybenzylsulfanyl)-2H-1,4-benzoxazin-3(4H)-one

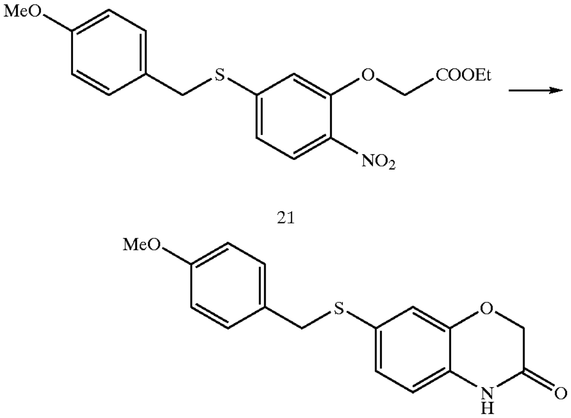

21

Example 12

Using the general method described in Example 1, 7-(4-methoxy-benzylsulfanyl)-2H-1,4-benzoxazin-3(4H)-one was obtained from 21 (1.89 g; 5.0 mmol) after trituration with EtOAc. The product was a beige solid (1.32 g). Yield: 87% $^1$H NMR spectrum (DMSO $d_6$): 3.71 (s, 3H); 4.10 (s, 2H); 4.55 (s, 2H); 6.80 (d, 1H); 6.84 (m, 2H); 6.91 (dd, 1H); 6.92 (d, 1H); 7.22 (m, 2H); 10.70 (s, 1H). LCMS-ESI: 300 $[M+H]^-$

| | | | | | |
|---|---|---|---|---|---|
| Elemental analysis: | Found | C 63.58 | H 5.03 | N 4.72 | S 10.27 |
| $C_{16}H_{15}NO_3S$ | Requires | C 63.77 | H 5.02 | N 4.65 | S 10.64 |

The starting material was prepared as follows:

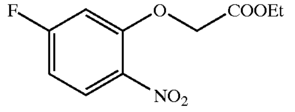

3

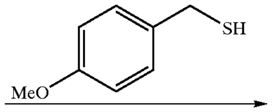

22

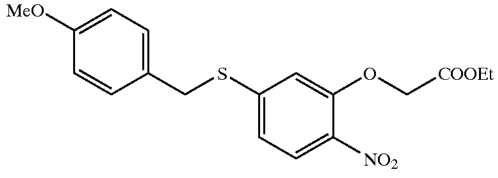

21

Using the general method described for the starting material in Example 9, 21 (1.89 g) was obtained from 3 (1.215 g; 5 mmol) and 22 (0.77 g; 5 mmol). Yield: 99% $^1$H NMR spectrum ($CDCl_3$): 1.29 (t, 3H); 3.80 (s, 3H); 4.15 (s, 2H); 4.26 (q, 2H); 4.67 (s, 2H); 6.77 (d, 1H); 6.86 (m, 2H); 6.93 (dd, 1H); 7.27 (m, 2H); 7.83 (d, 1H). LCMS-ESI: 378 $[MH]^+$

EXAMPLE 13

7-(4-Hydroxybenzylsulfanyl)-2H-1,4-benzoxazin-3(4H)-one

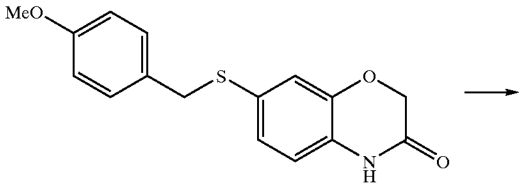

Example 12

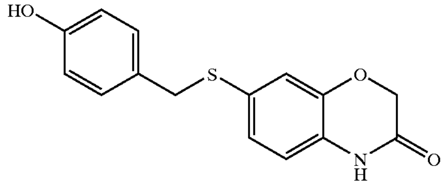

Example 13

A solution of 7-(4-methoxy-benzylsulfanyl)-2H-1,4-benzoxazin-3(4H)-one(150 mg; 0.5 mmol) in $CH_2Cl_2$ (2 ml) was treated with $BBr_3$ (350 mg; 1.5 mmol). The mixture was stirred at room temperature overnight. After evaporation to dryness the residue was taken up in EtOAc and water. The organic phase was washed with water, brine and dried over MgSO4. The residue was triturated with EtOAc, filtered and dried to give 7-(4-hydroxybenzylsulfanyl)-2-H-1,4-benzoxazin-3(4H)-one as a beige solid (149 mg), Melting point 207–209° C. Yield: 100% $^1$H NMR spectrum (DMSO $d_6$): 4.07(s, 2H); 4.56 (s, 2H); 6.68 (m, 2H); 6.81 (d, 1H); 6.91 (m, 2H); 7.11 (d, 2H); 9.35 (s, 1H); 10.72 (s, 1H). LCMS-ESI: 288 $[MH]^+$

| Elemental analysis: | Found | C 62.24 | H 4.77 | N 4.81 | S 10.01 |
|---|---|---|---|---|---|
| $C_{15}H_{13}NO_3S$; 0.2 EtOAc | Requires | C 62.23 | H 4.83 | N 4.59 | S 10.51 |

EXAMPLE 14

7-(4-Methoxyanilino)-2H-1,4-benzoxazin-3(4H)-one

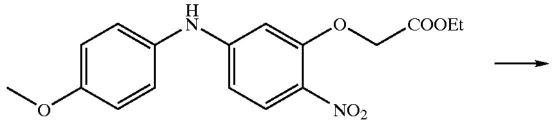

23

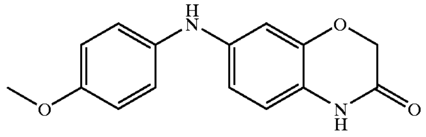

Example 14

Using the general method described for Example 1, 7-(4-methoxyanilino)-2H-4-benzoxazin-3(4H)-one was obtained from 23 (500 mg; 1.4 mmol) after purification by flash chromatography eluting with increasingly polar mixtures of EtOAc/hexanes (50 to 60% EtOAc). The product was a beige solid (363 mg), Melting point 174–175° C. Yield: 93% $^1$H NMR spectrum (DMSO $d_6$): 3.72 (s, 3H); 4.50 (s, 2H); 6.52 (d, 1H); 6.55 (dd, 1H); 6.74 (d, 1H); 6.86 (m, 2H); 6.99 (m, 2H); 7.73 (s, 1H); 10.46 (s, 1H). LCMS-ESI: 271 $[MH]^+$

| Elemental analysis: | Found | C 66.50 | H 5.14 | N 10.31 |
|---|---|---|---|---|
| $C_{15}H_{14}N_2O_3$ | Requires | C 66.66 | H 5.22 | N 10.36 |

The starting material was prepared as follows:

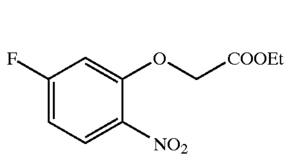

3

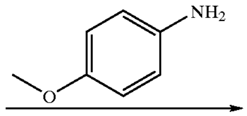

24

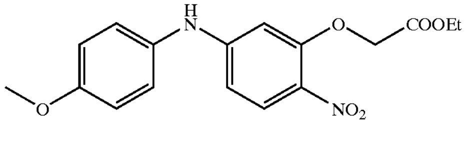

23

Compound 3 (1.21 g; 5 mmol) and compound 24 (0.61 g; 5 mmol) were disclosed in N,N-dimethylacetamide (10 ml) under argon and the mixture was heated at 90° C. and stirred for 14 hours. The mixture was further heated at 100° C. for 3 days and then allowed to cool. The mixture was poured in water and extracted with EtOAc (3×). The organic phase was washed with water, brine and dried over $MgSO_4$.

The residue (1.75 g) was purified by flash chromatography eluting with increasingly polar mixtures of EtOAc/hexanes (20 to 40% EtOAc). The appropriate fractions were evaporated to give 23 as a gum (500 mg). Yield: 30% $^{1}H$ NMR spectrum ($CDCl_3$): 1.26 (t, 3H); 3.83 (s, 3H); 4.23 (q, 2H); 4.65 (s; 2H); 6.15 (s, 1H); 6.24 (d, 1H); 6.39 (dd, 1H); 6.92 (m, 2H); 7.12 (m, 2H); 7.96 (d, 1H). LCMS-ESI: 347 $[MH]^+$

EXAMPLE 15

7-(4-Hydroxyanilino)-2H-1,4-benzoxazin-3(4H)-one

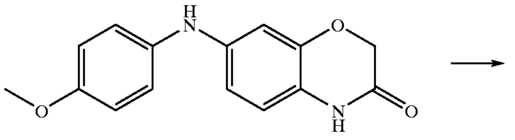

Example 14

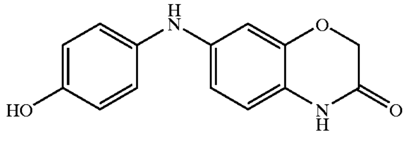

Example 15

A solution of 7-(4-methoxyanilino)-2H-1,4-benzoxazin-3(4H)-one (135 mg; 0.5 mmol) in $CH_2Cl_2$ (2 ml) was treated with $BBr_3$ (350 mg; 1.5 mmol). The mixture was stirred at room temperature for overnight. After evaporation to dryness the residue was taken up in EtOAC and saturated aqueous $NaHCO_3$. The organic phase was washed with water, brine and dried over $MgSO_4$. The residue (147 mg) was triturated with EtOAc, filtered and dried to give 7-(4-hydroxyanilino)-2H-1,4-benzoxazin-3-(4H)-one as a magenta solid (120 mg), Melting point 270–275° C. Yield: 94% $^{1}H$ NMR spectrum (DMSO $d_6$): 4.48(s, 2H); 6.46 (d, 1H); 6.48 (dd, 1H); 6.68–6.72 (m, 3H); 6.89 (m, 2H); 7.56 (s, 1H); 8.98 (s, 1H); 10.42 (s, 1H). LCMS-ESI: 256 $[MH]^+$

| | | | | |
|---|---|---|---|---|
| Elemental analysis: | Found | C 65.07 | H 4.83 | N 10.55 |
| $C_{14}H_{12}N_2O_3$; 0.1 EtOAc | Requires | C 65.25 | H 4.78 | N 10.57 |

EXAMPLE 16

7-(4-Aminophenoxy)-2H-1,4-benzoxazin-3-(4H)-one

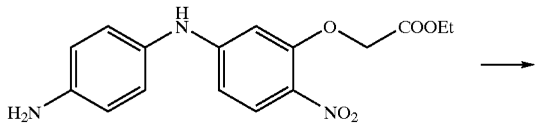

25

-continued

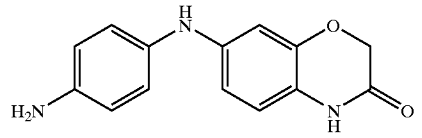

Example 16

Using the general method described in Example 1, 7-(4-aminophenoxy)-2H-1,4-benzoxazin-3(4H)-one was obtained from 25 (690 mg; 2.0 mmol) after purification by flash chromatography eluting with increasingly polar mixtures of EtOAc/hexanes (70 to 100% EtOAc). The product was a white solid (243 mg), Melting point 201–202° C. Yield: 46% $^{1}H$ NMR spectrum (DMSO $d_6$): 4.52 (s, 2H); 4.95 (s, 2H); 6.44 (d, 1H); 6.45 (dd, 1H); 6.56 (m, 2H); 6.73 (m, 2H): 6.80 (d, 1H); 10.58 (s, 1H). LCMS-ESI: 255 $[M-H]^-$

| | | | | |
|---|---|---|---|---|
| Elemental analysis: | Found | C 65.06 | H 4.58 | N 10.85 |
| $C_{14}H_{12}N_2O_3$; 0.1 $H_2O$ | Requires | C 65.16 | H 4.77 | N 10.86 |

The starting material was prepared as follows:

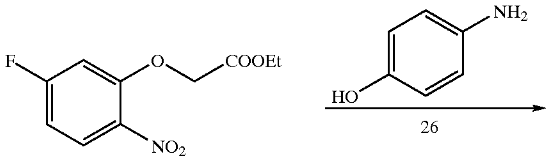

3

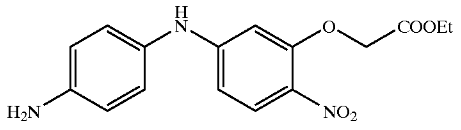

25

Compound 26 (1.09 g; 10 mmol) was dissolved in N,N-dimethylacetamide (10 ml) under argon and was treated with NaH (450 mg; 60% in oil; 11 mmol). The mixture was stirred for 1 hour and a solution of compound 3 (2.43 g; 10 mmol) was added. The mixture was heated at 60° C. and stirred for 2 hours then further heated at 85° C. for 3.5 hours and then allowed to cool. The mixture was poured into water and extracted with EtOAc (3×). The organic phase was washed with water, saturated aqueous $NaHCO_3$, then brine and dried over $MgSO_4$.

The residue (3 g) was purified by flash chromatography eluting with increasingly polar mixtures of EtOAc/hexanes (50 to 60% EtOAc). The appropriate fractions were evaporated to give 25 as yellow oil (690 mg). Yield: 20% $^{1}H$ NMR spectrum ($CDCl_3$): 1.28 (t, 3H); 3.70 (s, 2H); 4.25 (q, 2H); 4.69 (s, 2H); 6.46 (d, 1H); 6.51 (dd, 1H); 6.71 (m, 2H); 6.87 (m, 2H); 7.94 (d, 1H). LCMS-ESI: 333 $[MH]^+$

EXAMPLE 17

7-(3-Aminophenoxy)-2H-1,4-benzoxazin-3(4H)-one

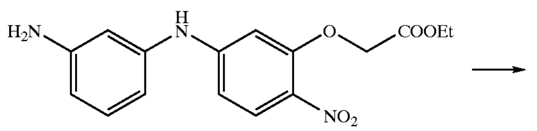

27

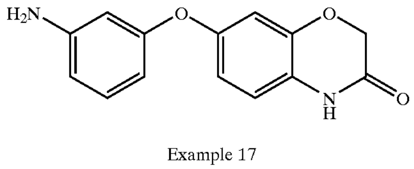

Example 17

Using the general method described for Example 1, 7-(3-aminophenoxy)-2H-1,4-benzoxazin-3-(4H)-one was obtained from 27 (800 mg; 2.4 mmol) after purification by flash chromatography eluting with increasingly polar mixtures of EtOAc/hexanes (50 to 70% EtOAc). The product was a white solid (239 mg), Melting point 209–210° C. Yield: 39% $^1$H NMR spectrum (DMSO $d_6$): 4.56 (s, 2H); 5.19 (s, 2H); 6.09 (m, 2H); 6.14 (t, 1H); 6.29 (m, 1H); 6.59 (m, 2H); 6.86 (m, 1H); 6.96 (t, 1H); 10.66 (s, 1H) LCMS-ESI: 255 [M−H]$^-$

| Elemental analysis: | Found | C 65.99 | H 4.72 | N 11.02 |
|---|---|---|---|---|
| $C_{14}H_{12}N_2O_3$ | Requires | C 65.62 | H 4.72 | N 10.93 |

The starting material was prepared as follows:

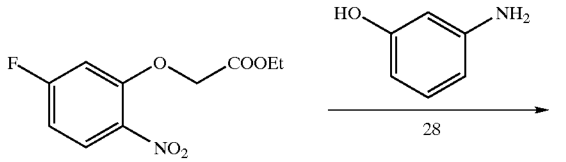

3

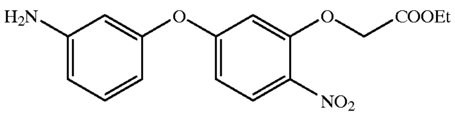

27

Using the general method described for the starting material in Example P, 27 (1.0 g) was obtained as a yellow oil from 3 (2.43 g; 10 mmol) and 28 (1.09 g; 10 mmol) after purification by flash chromatography eluting with increasingly polar mixtures of EtOAc/hexanes (40 to 50% EtOAc). Yield: 30% $^1$H NMR spectrum ($CDCl_3$): 1.28 (t, 3H); 3.82 (s, 2H); 4.25 (q, 2H); 4.70 (s, 2H); 6.36 (t, 1H); 6.41 (dd, 1H); 6.5–6.6 (m, 3H); 7.16 (t, 1H); 7.94 (d, 1H). LCMS-ESI: 333 [MH]$^+$

EXAMPLE 18

7-(2-Aminophenoxy)-2H-1,4-benzoxazin-3(4H)-one

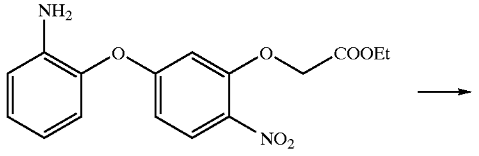

29

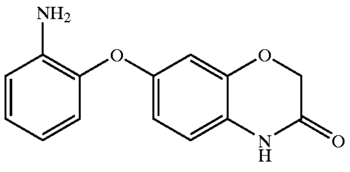

Example 18

Using the general method described in Example 1, 7-(2-aminophenoxy)-2H-1,4-benzoxazin-3-(4H)-one was obtained from 29 (400 mg; 1.2 mmol) after purification by flash chromatography eluting with increasingly polar mixtures of EtOAc/hexanes (50 to 70% EtOAc). The product was a light beige solid (201 mg), Melting point 149–150° C. Yield: 60% $^1$H NMR spectrum (DMSO $d_6$): 4.53 (s, 2H); 4.87 (s, 2H); 6.49–6.55 (m, 3H); 6.75–6.85 (m, 3H); 6.90 (t, 1H); 10.61 (s, 1H). LCMS-ESI: 255 [M−H]$^-$

| Elemental analysis: | Found | C 64.93 | H 4.86 | N 10.78 |
|---|---|---|---|---|
| $C_{14}H_{12}N_2O_3$; 0.2 $H_2O$ | Requires | C 64.71 | H 4.81 | N 10.78 |

The starting material was prepared as follows:

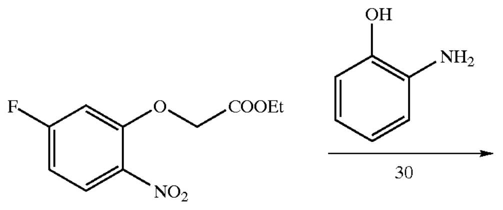

3

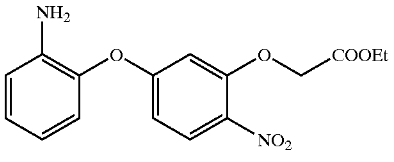

29

Using the general method described for the starting material in Example 16, 29 (1.93 g) was obtained as a yellow oil from 3 (2.43 g; 10 mmol) and 30 (1.09 g; 10 mmol) after purification by flash chromatography eluting with increasingly polar mixtures of EtOAc/hexanes (20 to 40% EtOAc). Yield: 60% $^1$H NMR spectrum ($CDCl_3$): 1.27 (t, 3H); 3.74 (s, 2H); 4.23 (q, 2H); 4.69 (s, 2H); 6.50 (d, 1H); 6.57 (dd, 1H); 6.77 (dt, 1H); 6.85 (dd, 1H); 6.92 (dd, 1H); 7.08 (dt, 1H); 7.95 (d, 1H). LCMS-ESI: 333 [MH]$^+$

EXAMPLE 19

7-(4-Acetylaminophenoxy)-2H-1,4-benzoxazin-3 (4H)-one

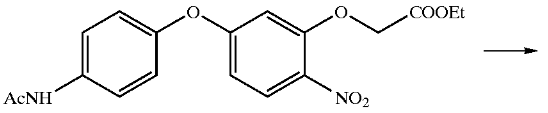

31

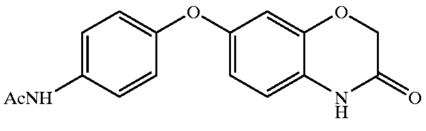

Example 19

Using the general method described for Example 1, 7-(4-acetylaminophenoxy)-2H-1,4-benzoxazin-3(4H)-one was obtained from 31 (980 mg; 2.6 mmol) after purification by flash chromatography eluting with increasingly polar mixtures of EtOAc/hexanes (80 to 100% EtOAc). The product was a pale cream solid (770 mg), Melting point 230–232° C. Yield: 99% $^1$H NMR spectrum (DMSO $d_6$): 2.02 (s, 3H); 4.56 (s, 2H); 6.57 (m, 2H); 6.86 (dd, 1H); 6.93 (m, 2H); 7.56 (m, 2H); 9.92 (s, 1H); 10.66 (s, 1H). LCMS-ESI: 297 $[M-H]^-$

| | | | | |
|---|---|---|---|---|
| Elemental analysis: | Found | C 63.46 | H 5.01 | N 9.16 |
| $C_{16}H_{14}N_2O_4$; 0.2 MeOH | Requires | C 63.86 | H 4.90 | N 9.19 |

The starting material was prepared as follows:

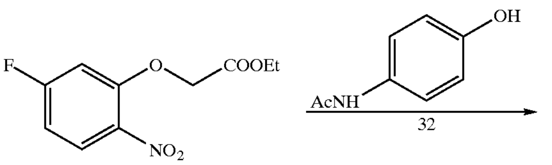

3

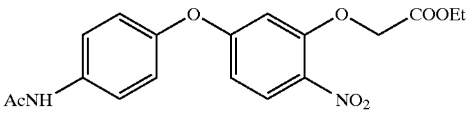

31

Using the general method described for the starting material in Example 3, except that N,N-dimethylacetamide was used as solvent and the mixture was heated at 110° C. for 18 hours, 31 (1.85 g) was obtained as a pale yellow oil from 3 (7.29 g; 30 mmol) and 32 (4.5 g; 30 mmol) after purification by flash chromatography eluting with increasingly polar mixtures of EtOAc/hexanes (60 to 80% EtOAc). Yield: 16% $^1$H NMR spectrum ($CDCl_3$): 1.27 (t, 3H); 2.20 (s, 3H); 4.25 (q, 2H); 4.70 (s, 2H); 6.53 (m, 2H); 7.03 (d, 2H); 7.31 (s, 1H); 7.56 (d, 2H); 7.95 (d, 1H); LCMS-ESI: 375 $[MH]^+$

| | | | | |
|---|---|---|---|---|
| Elemental analysis: | Found | C 56.92 | H 4.82 | N 7.37 |
| $C_{18}H_{18}N_2O_7$; 0.3 $H_2O$ | Requires | C 56.93 | H 4.94 | N 7.38 |

EXAMPLE 20

6-[2-(4-Toluidino)acetyl]-2H-1,4-benzoxazin-3(4H)-one

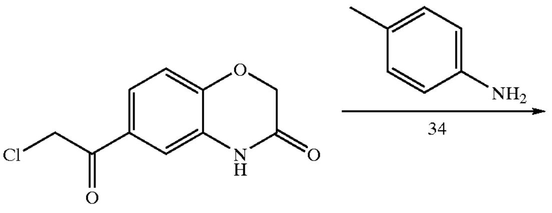

33

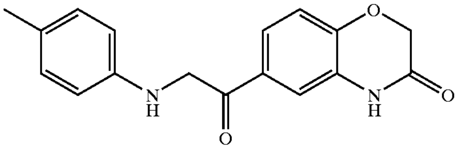

Example 20

A solution of 33 (226 mg; 1.0 mmol) and 34 (118 mg; 1.1 mmol) in acetone (10 ml) was treated with $K_2CO_3$ (276 mg; 2.0 mmol) and then KI (166 mg; 1.0 mmol). The mixture was stirred at room temperature for 2 days. Water was added and the precipitate filtered, washed with water and dried. The residue was was purified by flash chromatography eluting with $CH_2Cl_2$/EtOAc/MeOH (70/30/5). The appropriate fractions were evaporated to give 6-[2-(4-toluidino) acetyl]-2H-1,4-benzoxazin-3(4H)-one as a beige solid (60 mg). Yield: 20% $^1$H NMR spectrum (DMSO $d_6$): 2.16(s, 3H); 4.56(d, 2H); 4.71(s, 2H): 5.60 (t, 1H); 6.58 (d, 2H); 6.91 (d, 2H); 7.09 (d, 1H); 7.54 (d, 1H); 7.78 (dd, 1H); 10.88 (s, 1H). LCMS-ESI: 297 $[MH]^+$

EXAMPLE 21

6-[2-(4-Aminoanilino)acetyl]-2H-1,4-benzoxazin-3 (4-H)-one

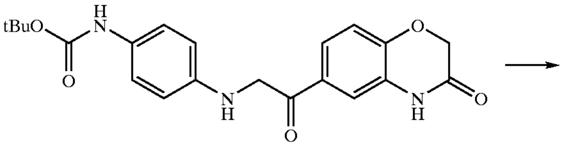

35

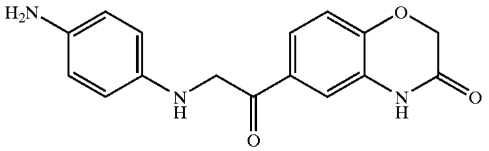

Example 21

Compound 35 (200 mg; 0.5 mmol) was taken up in a saturated solution of gaseous HCl in EtOAc (10 ml) and the mixture stirred for 3 days. The precipitate that remained was filtered washed with $Et_2O$ and dried to give 6-[2-(4-aminoanilino)acetyl]-2H-1,4-benzoxazin-3(4H)-one as a beige solid (180 mg).

Yield: 100%

$^1$H NMR spectrum (DSMO $d_6$): 4.62 (s, 2H); 4.70 (s, 2H); 6.72 (d, 2H); 7.09 (m, 3H); 7.53 (d, 1H); 7.76 (dd, 1H); 9.75 (br s, 3H); 10.90 (s, 1H).

LCMS-ESI: 296 [M-H]$^-$

| Elemental analysis: | | | | | |
|---|---|---|---|---|---|
| $C_{16}H_{15}N_3O_3$, | Found | C 51.25 | H 4.75 | N 11.05 | Cl 16.5 |
| 1.75 HCl, 0.7 $H_2O$ | Requires | C 51.42 | H 4.90 | N 11.24 | Cl 16.60 |

The starting material was prepared as follows:

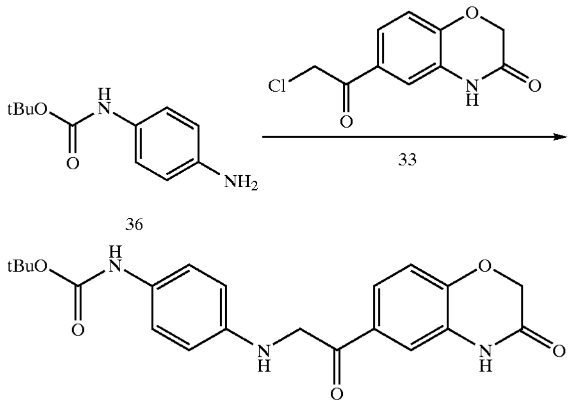

33

36

35

Compound 36 (1.04 g; 5 mmol) was dissolved in acetone (40 ml) and was treated with $K_2CO_3$ (1.38 g; 10 mmol) and KI (830 mg; 5 mmol). The mixture was stirred for 1 hour. A suspension of 33 (1.41 g; 5.25 mmol) in acetone (20 ml) was added and the mixture was heated under reflux for 1 hour. The cooled mixture was poured into water and extracted with EtOAc (3×). The organic phase was washed with water, brine and dried over $MgSO_4$.

The residue was purified by trituration in hot MeOH to give 35 as a yellow solid (1.16 g).

Yield: 58%

$^1$H NMR spectrum ($CDCl_3$): 1.44 (s, 9H); 4.54 (d, 2H); 4.69 (s, 2H); 5.53 (t, 1H); 6.58 (m, 2H); 7.08 (d, 1H): 7.14 (m, 2H): 7.53 (d, 1H); 7.75 (dd, 1H); 8.82 (s, 1H); 10.87 (s, 1H).

LCMS-ESI: 398 [MH]$^+$

EXAMPLE 22

7-(4-L-a-Glutamyl-phenylsulfanyl)-2H-1,4-benzoxazin-3(4H)-one

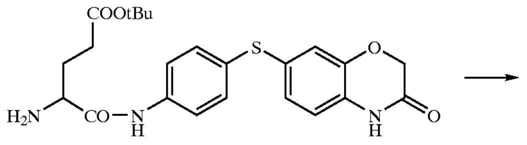

37

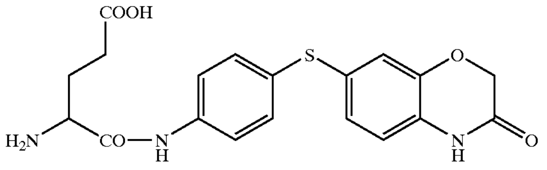

Example 22

A solution of 37 (160 mg; 0.35 mmol) in EtOAc (3 ml) was treated with a saturated solution of gaseous HCl in EtOAc (10 ml). The mixture was stirred at room temperature overnight. After evaporation to dryness, the residue was taken up in water and purified by reverse phase chromatography on an OASIS resin eluting with increasingly lipophilic mixtures of MeCN/water (0 to 100% MeCN), buffered with 1% aqueous HCl. The appropriate fractions were evaporated and dried to give the hydrochloride of 7-(4-L-a-glutamyl-benzylsulfanyl)-2H-1,4-benzoxazin-3(4H)-one as a white solid (113 mg).

Yield: 72%

$^1$H NMR spectrum (DMSO $d_6$, $CD_3OD$): 2.09 (m, 2H); 2.42 (m, 2H); 4.04 (m, 1H); 4.56 (s, 2H); 6.86 (d, 1H); 6.92 (m, 2H); 7.32 (d, 2H); 7.63 (d, 2H); 10.78 (s, 1H).

LCMS-ESI: 400 [M-H]$^-$

The starting material was prepared as follows:

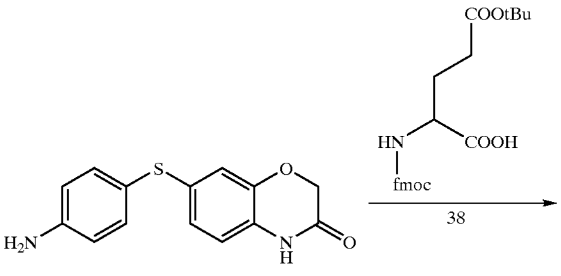

Example 3

38

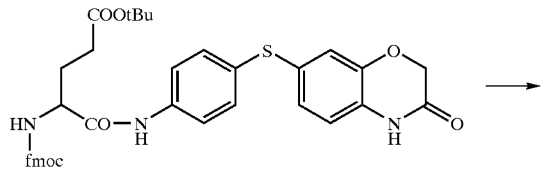

39

-continued

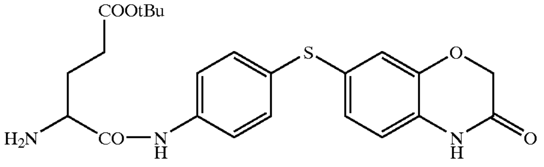

37

A solution of Example 3 (7-[(4-aminophenyl)sulfanyl]-2H-1,4-benzoxazin-3(4H)-one) (275 mg; 1.0 mmol) and 38 (850 mg; 2.0 mmol) in $CH_2Cl_2$ (10 ml) was treated with EDCI (480 mg; 2.5 mmol) and a catalytic quantity of DMAP (10 mg). The mixture was stirred at room temperature for 1 hour. The mixture was directly purified by flash chromatography eluting with $CH_2Cl_2$/EtOAc (50/50). The appropriate fractions wee evaporated to give 39 as a white solid (648 mg).

Yield: 95%

$^1$H NMR spectrum ($CDCl_3$): 1.46 (s, 9H); 2.03 (m, 1H); 2.17 (m, 1H); 2.41 (m, 1H); 2.57 (m, 1H); 4.20 (t, 1H); 4.40 (m, 3H); 4.58 (s, 2H); 6.08 (m, 1H); 6.72 (d, 1H); 6.90 (m, 2H); 7.26 (m, 2H); 7.31 (d, 2H); 7.38 (t, 2H); 7.51 (d, 2H): 7.57 (t, 2H); 7.74 (d, 2H); 8.67 (s, 1H); 8.84 (s, 1H).

A solution of 39 (1.08 g; 1.4 mmol) in $CH_2CHl_2$ (40 ml) and DMF (5 ml) was treated with piperidine (20 ml). The mixture was stirred at room temperature for 1 hour. After evaporation to dryness, the residue was purified by flash chromatography eluting with increasingly polar mixtures of MeOH/$CH_2Cl_2$ (0 to 10% MeOH). The appropriate fractions were evaporated to give 37 as a white solid (389 mg).

Yield: 53%

$^1$H NMR spectrum (DMSO $d_6$): 1.40 (s, 9H); 1.67 (m, 1H); 1.86 (m, 1H); 2.32 (m, 2H); 3.32 (m, 1H); 4.57 (s, 2H); 6.82 (d, 1H); 6.90 (m, 2H); 7.32 (d, 2H); 7.68 (d, 2H); 10.78 (s, 1H). LCMS-ESI: 456 $[M-H]^+$

EXAMPLE 23

7-(3-L-a-Glutamyl-phenylsulfanyl)-2H-1,4-benzoxazin-3(4H)-one

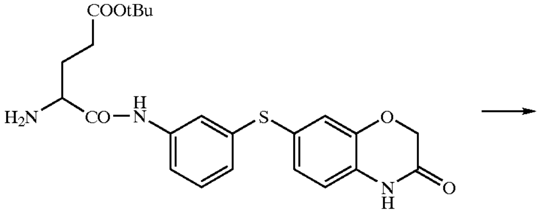

40

-continued

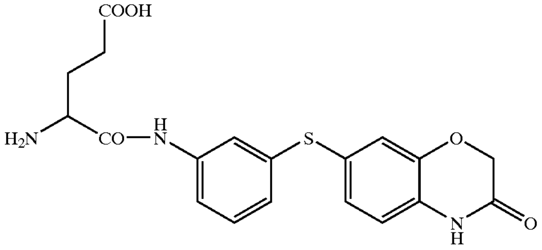

Example 23

Using the general method described in Example 22, 7-(3-L-a-glutamyl-phenylsulfanyl)-2H-1,4-benzoxazin-3(4H)-one (563 mg) was obtained as a white solid from 40 (640 mg; 1.4 mmol) after purification by reverse phase chromatography eluting with increasingly lipophilic mixtures of MeCN/water (0 to 100% MeCN), buffered with 1% aqueous HCl.

Yield: 99%

$^1$H NMR spectrum (DMSO $d_6$): 2.07 (m, 2H); 2.39 (m, 2H); 4.01 (m, 1H); 4.61 (s, 2H); 6.97 (m, 3H); 7.07 (dd, 1H); 7.33 (t, 1H); 7.50 (d, 1H); 7.58 (s, 1H); 8.37 (m, 2H); 10.81 (s, 1H); 10.91 (s, 1H).

LCMS-ESI: 400 $[M-H]^-$

| | | | | | |
|---|---|---|---|---|---|
| Elemental analysis: | Found | C 49.99 | H 4.79 | N 9.29 | S 6.66 |
| $C_{19}H_{19}N_3O_5S$; 1.2 HCl 0.5 $H_2O$ | Requires | C 50.24 | H 4.70 | N 9.25 | S 7.06 |

The starting material was prepared as follows:

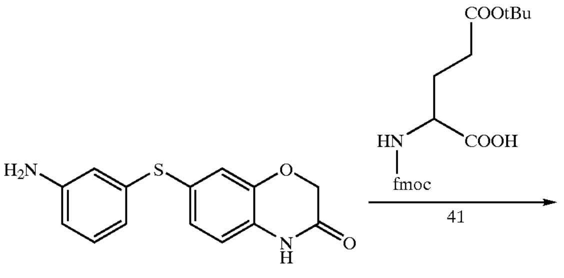

Example 5

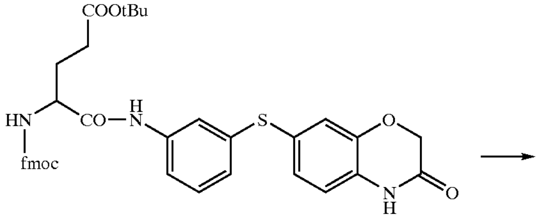

42

-continued

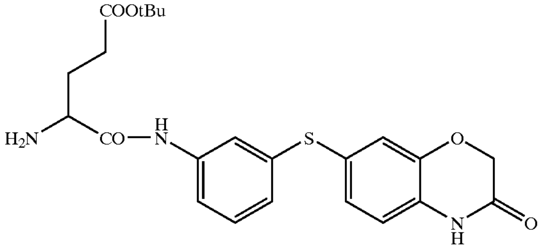

40

Using the general method described for the starting material in Example 22, 42 (2.43 g) was obtained as a white solid from Example 5 (7-[(3-Aminophenyl)sulfanyl]-2H-1,4-benzoxazin-3(4H)-one) (820 mg; 3.0 mmol) and 41 (2.3 g; 5.4 mmol) after purification by flash chromatography eluting with increasingly polar mixtures of EtOAc/hexanes (40 to 70% EtOAc).

Yield: 100%

$^1$H NMR spectrum ($CDCl_3$): 1.45 (s, 9H); 2.01 (m, 1H); 2.13 (m, 1H); 2.38 (m, 1H); 2.51 (m, 1H); 4.17 (t, 1H); 4.38 (m, 3H); 4.55 (s, 2H); 6.00 (m, 1H); 6.71 (d, 1H); 6.97 (dd, 1H); 7.00 (d, 1H); 7.05 (d, 1H); 7.24 (m, 3H); 7.37 (t, 2H); 7.48 (d, 2H); 7.55 (t, 2H); 7.73 (d, 2H); 8.60 (s, 1H); 8.76 (s, 1H).

LCMS-ESI: 680 $[MH]^+$ and similarly 40 (1.17 g) was obtained as a white solid from 42 (2.4 g; 3.5 mmol) after purification by flash chromatography eluting with increasingly polar mixtures of MeOH/$CH_2Cl_2$ (0 to 10% MeOH).

Yield: 73%

$^1$H NMR spectrum (DMSO $d_6$): 1.40 (s, 9H); 1.65 (m, 1H); 1.85 (m, 1H); 2.29 (m, 2H); 3.30 (m, 1H); 4.61 (s, 2H); 6.96 (m, 3H); 7.03 (dd, 1H); 7.29 (t, 1H); 7.53 (d, 2H) 7.65 (s, 1H); 10.85 (s, 1H).

LCMS-ESI: 456 $[M-H]^-$

EXAMPLE 24

7-(4-Phosphonophenoxy)-2H-1,4-benzoxazin-3(4H)-one

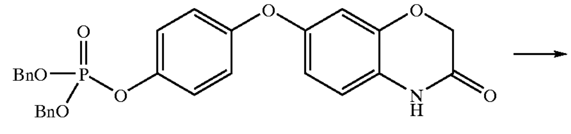

43

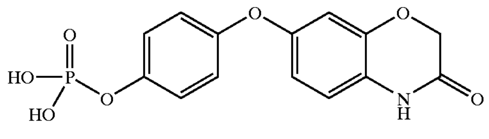

Example 24

A solution of 43 (310 mg; 0.6 mmol) in EtOAc (5 ml) and MeOH (5 ml) was hydrogenated at 30 psi at room temperature for 30 minutes. After filtration and evaporation to dryness, the residue was taken up in water and purified by reverse phase chromatography on an OASIS resin eluting with increasingly lipophilic mixtures of MeCN/water (0 to 50% MeCN), buffered with 1% aqueous HCl. The appropriate fractions were adjusted to pH 7.0 with aqueous NaOH (0.1N) and freeze-dried to give the disodium salt of 7-(4-phosphonophenoxy)-2H-1,4-benzoxazin-3(4-H)-one as a white solid (200 mg).

Yield: 87%

$^1$H NMR spectrum (DMSO $d_6$, $CD_3OD$): 4.52 (s, 2); 6.56 (m, 2H); 6.88 (m, 3H); 7.14 (d, 2H); 10.54 (s, 1H).

LCMS-ESI: 336 $[M-H]^-$

| | | | | |
|---|---|---|---|---|
| Elemental analysis: | Found | C 42.30 | H 3.11 | N 3.63 |
| $C_{14}H_{10}NO_7P$; 1.8 Na 1.2 $H_2O$ | Requires | C 42.19 | H 3.15 | N 3.51 |

The starting material was prepared as follows:

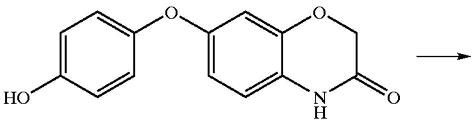

Example 2

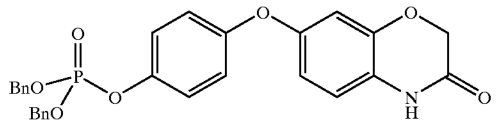

43

Example 2 (7-(4-hydroxyphenoxy)-2H-1,4-benzoxazin-3(4H)-one) (514 mg; 2 mmol) was dissolved in $CH_3CN$ (20 ml) under argon and was treated successively with $CCl_4$ (1 ml), diisopropylethylamine (730 uL; 4.2 mmol), DMAP (10 mg) and dibenzyl phosphite (1.320 ml; 6 mmol). The mixture was stirred at room temperature for 24 hours. The mixture was evaporated, poured into aqueous. $KH_2PO_4$ and extracted with $CH_2Cl_2$.

The residue was purified by flash chromatography eluting with increasingly polar mixtures of EtOAc/$CH_2Cl_2$ (20 to 30% EtOAc). The appropriate fractions were evaporated to give 43 as a white solid (570 mg).

Yield: 55%

$^1$H NMR spectrum (DMSO $d_6$): 4.60 (s, 2H); 5.16 (s, 2H); 5.18 (s, 2H); 6.64 (m, 2H); 6.91 (d, 1H); 7.00 (m, 2H); 7.20 (m, 2H); 7.39 (m, 10H); 10.72 (s, 1H).

LCMS-ESI: 516$[M-H]^-$

What is claimed is:

1. A compound of Formula (II) or a salt, pro-drug or solvate thereof, wherein:

Formula (II)

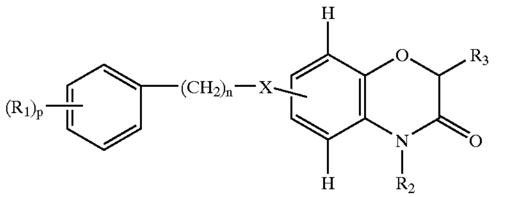

X is selected from: —O—, —S—, —S(O)—, —$S(O_2)$—, —$N(R_4)$— or —$N(R_4)CH_2C(O)$—;

$R_1$ is independently selected from: amino, halo, hydroxy, —$OPO_3H_2$, $C_{1-4}$alkyl, $C_{1-4}$alkoxy, N-$C_{1-4}$-alkylamino, N,N-di-$C_{1-4}$alkylamino, $C_{1-4}$alkanoylamino or $C_{1-4}$alkylthio wherein the amino group is optionally substituted by an amino acid residue and the hydroxy group is optionally esterified;

$R_2$ is selected from; hydrogen or $C_{1-4}$alkyl;

$R_3$ is selected from; hydrogen or $C_{1-4}$alkyl;

$R_4$ is selected from; hydrogen or $C_{1-4}$alkyl;

n is 0, 1 or 2; and p is 0, 1, 2 or 3;

with the proviso that the following compounds are excluded:

6-benzyloxy-2H-1,4-benzoxazin-3(4H)-one;

7-benzyloxy-2H-1,4-benzoxazin-3(4H)-one;

2-methyl-7-benzyloxy-2H-1,4-benzoxazin-3(4H)-one;

2,4-dimethyl-7-benzyloxy-2H-1,4-benzoxazin-3(4H)-one;

2-methyl-7-(3,5-dichlorobenzyloxy)-2H-1,4-benzoxazin-3(4H)-one;

2,4-dimethyl-7-(3,5-dichlorobenzyloxy)-2H-1,4-benzoxazin-3(4H)-one;

7-phenylthio-2H-1,4-benzoxazin-3(4H)-one;

4-methyl-7-phenylthio-2H-1,4-benzoxazin-3(4H)-one;

4-methyl-7-phenylsulfinyl-2H-1,4-benzoxazin-3(4H)-one; and 6-phenylsulfonyl-2H-1,4-benzoxazin-3(4H)-one.

2. A compound according to claim 1 wherein $R_1$ is amino, $C_{1-4}$alkoxy, hydroxy or —$OPO_3H_2$, wherein the amino group is optionally substituted by an amino acid residue and the hydroxy group is optionally esterified.

3. A compound according to claim 2 wherein the amino acid residue is independently derived from; glutamic acid, serine, threonine, arginine, glycine, alanine, β-alanine or lysine.

4. A compound according to claim 1 wherein X is selected from: —O—, —S— or —$N(R_4)$—.

5. A compound according to claim 1 or 4 wherein $R_2$ is hydrogen.

6. A compound selected from:

7-[(2-aminophenyl)sulfanyl]-2H-1,4-benzoxazin-3(4H)-one;

7-(3-aminophenyl)-2H-1,4-benzoxazin-3(4H)-one;

6-[2-(4-toluidino)acetyl]-2H-1,4-benzoxazin-3(4H)-one;

7-[(3-aminophenyl)sulfanyl]-2H-1,4-benzoxazin-3(4H)-one; and

7-[(4-hydroxyphenyl)sulfanyl]-2H-1,4-benzoxazin-3(4H)-one;

or salt, pro-drug or solvate thereof.

7. A pharmaceutical composition comprising a pharmaceutically acceptable diluent or carrier and a compound of Formula (I), wherein:

Formula (I)

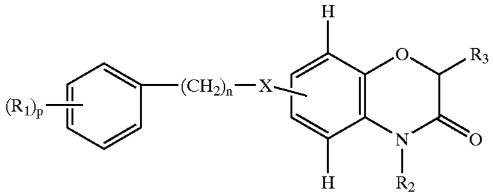

X is selected from: —O—, —S—, —S(O)—, —$S(O_2)$—, —$N(R_4)$—, or —$N(R_4)CH_2C(O)$—;

$R_1$ is independently selected from: amino, halo, hydroxy, —$OPO_3H_2$, $C_{1-4}$alkyl, $C_{1-4}$alkoxy, N-$C_{1-4}$-alkylamino, N,N-di-$C_{1-4}$-alkylamino, $C_{1-4}$alkanoylamino or $C_{1-4}$alkylthio wherein the amino group is optionally substituted by an amino acid residue and the hydroxy group is optionally esterified;

$R_2$ is selected from: hydrogen or $C_{1-4}$alkyl;

$R_3$ is selected from: hydrogen or $C_{1-4}$alkyl;

$R_4$ is selected from: hydrogen or $C_{1-4}$alkyl;

n is 0, 1 or 2; and p is 0, 1, 2 or 3;

or a pharmaceutically-acceptable salt, pro-drug or solvate thereof.

8. A pharmaceutical composition comprising a compound according to claim 1, 4 or 6 in admixture with a pharmaceutically acceptable diluent or carrier.

9. A process for preparing a compound of Formula (I) or salt, pro-drug or solvate thereof, Formula (I)

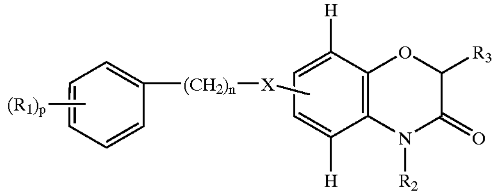

X is selected from: —O—, —S—, —S(O)—, —$S(O_2)$—, —$N(R_4)$—, or —$N(R_4)CH_2C(O)$—;

$R_1$ is independently selected from: amino, halo, hydroxy, —$OPO_3H_2$, $C_{1-4}$alkyl, $C_{1-4}$alkoxy, N-$C_{1-4}$alkylamino, N,N-di-$C_{1-4}$alkylamino, $C_{1-4}$alkanoylamino or $C_{1-4}$alkylthio wherein the amino group is optionally substituted by an amino acid residue and the hydroxy group is optionally esterified;

$R_2$ is selected from: hydrogen or $C_{1-4}$alkyl;

$R_3$ is selected from: hydrogen or $C_{1-4}$alkyl;

$R_4$ is selected from; hydrogen or $C_{1-4}$alkyl;

n is 0, 1 or 2; and p is 0, 1, 2 or 3;

which process comprises:

a) for compounds wherein X is —O—, —S— or —$N(R_4)$—, reacting a compound of Formula (A) with a compound of Formula (B), Formula (A)

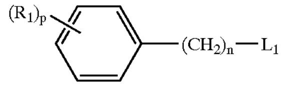

Formula (B)

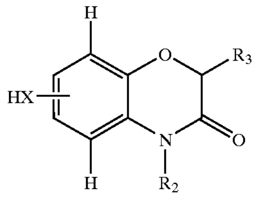

wherein $L_1$ is a leaving group;

b) for compounds wherein $R_2$ is hydrogen, reduction of a compound of Formula (C), wherein $R_6$ is hydrogen or an alkyl chain, Formula (C)

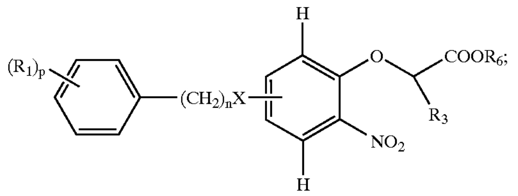

c) for compounds wherein $R_2$ is $C_{1-4}$alkyl, reacting a compound of Formula (I) wherein $R_2$ is hydrogen with a suitable alkylahalide;

d) for compounds wherein X is —S(O)—, —S($O_2$)—, oxidising a compound of Formula (D), Formula (D)

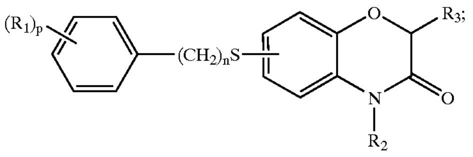

e) for compounds wherein X is —N($R_4$)$CH_2$C(O)—, reacting a compound of Formula (E) with a compound of Formula (F), Formula (E)

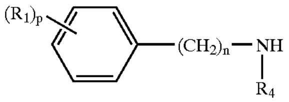

Formula (F)

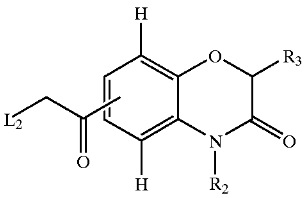

wherein $L_2$ is a leaving group;

and thereafter is necessary;

i) converting a compound of Formula (I) into another compound of Formula (I):

ii) removing any protecting groups;

iii) forming a salt, pro-drug or solvate.

* * * * *